United States Patent [19]
Miller et al.

[11] Patent Number: 6,136,598
[45] Date of Patent: Oct. 24, 2000

[54] *MUS DUNNI* ENDOGENOUS RETROVIRAL PACKAGING CELL LINES

[75] Inventors: A. Dusty Miller; Greg Wolgamot; Lynn Bonham, all of Seattle, Wash.

[73] Assignee: Fred Hutchinson Cancer Research Center, Seattle, Wash.

[21] Appl. No.: 09/075,272

[22] Filed: May 8, 1998

Related U.S. Application Data

[60] Provisional application No. 60/046,140, May 9, 1997.

[51] Int. Cl.$^7$ ........................................................ C12N 5/10
[52] U.S. Cl. ............................................. 435/325; 435/355
[58] Field of Search ..................................... 435/325, 355

[56] References Cited

U.S. PATENT DOCUMENTS

| | | |
|---|---|---|
| 4,861,719 | 8/1989 | Miller . |
| 5,219,740 | 6/1993 | Miller et al. . |
| 5,470,726 | 11/1995 | Miller et al. . |
| 5,652,130 | 7/1997 | Kriegler et al. . |
| 5,739,018 | 4/1998 | Miyanohara et al. . |

OTHER PUBLICATIONS

Berendsen, Science, vol. 282, pp. 642–643, Oct. 1998.
Bayle et al., "High–Efficiency Gene Transfer to Primary Monkey Airway Epithelial Cells with Retrovirus Vectors Using the Gibbon Ape Leukemia Virus Receptor," *Human Gene Ther.* 4:161–170 (1993).
Burns et al., "Vesicular Stomatitis Virus G Gylcoprotein Pseudotyped Retroviral Vectors: Concentration to Very High Titer and Efficient Gene Transfer into Mammalian and Nonmammalian Cells," *Proc. Natl. Acad. Sci. USA* 90:8033–8037 (Sep., 1993).
Kavanaugh et al., "Cell–Surface Receptors for Gibbon Ape Leukemia Virus and Amphotropic Murine Retrovirus are Inducible Sodium–Dependent Phosphate Symporters," *Proc. Natl. Acad. Sci. USA* 91:7071–7075 (Jul., 1994).
Lin et al., "Integration and Germ–Line Transmission of a Pseudotyped Retroviral Vector in Zebrafish," *Science* 265:666–669 (Jul. 29, 1994).
Pescini et al., "Inducible Inhibition of Eukaryotic Gene Expression," *Biochem. Biophys. Res. Commun.* 202:1664–1667 (Aug. 15, 1994).
Von Kalle et al., "Increased Gene Trasnfer into Human Hematopoietic Progenitor Cells by Extended In Vitro Exposure to a Pseudotyped Retroviral Vector," *Blood* 84:2890–2897 (Nov. 1, 1994).
Kasahara et al., "Tissue–Specific Targeting of Retroviral Vectors Thorugh Ligand–Receptor Interactions," *Science* 266:1373–1376 (Nov. 25, 1994).
Miller and Miller, "A Family of Retroviruses that Utilize Related Phosphate Transporters for Cell Entry," *J. Virol.* 68:8270–8276 (Dec., 1994).

Somia et al., "Generation of Targeted Retroviral Vectors by Using Single–Chain Variable Fragment: An Approach to in vivo Gene Delivery," *Proc. Natl. Acad. Sci. USA* 92:7570–7574 (Aug., 1995).
Sorge et al., "Amphotropic Retrovirus Vector System for Human Cell Gene Transfer," *Mol. Cell. Biol.* 4:1730–1737 (Sep., 1984).
Cone and Mulligan, "High–Efficiency Gene Transfer into Mammalian Cells: Generation of Helper–Free Recombinant Retrovirus with Broad Mammalian Host Range," *Proc. Natl. Acad. Sci. USA*, 81:6349–6353 (Oct., 1984).
Lander and Chattopadhyay, "A *Mus dunni* Cell Line that Lacks Sequences Closely Related to Endogenous Murine Leukemia Viruses and Can be Infected by Ecotropic, Amphotropic, Xenotropic and Mink Cell Focus–Forming Viruses," *J. Virol.* 52:695–698 (Nov., 1984).
Miller et al., "Generation of Helper–Free Amphotropic Retroviruses that Transduce a Dominant–Acting, Methotrexate–Resistant Dihydrofolate Reductase Gene," *Mol. Cell. Biol.*, 5:431–437 (Mar., 1985).
Miller and Buttimore, "Redesign of Retrovirus Packaging Cell Lines to Avoid Recombination Leading to Helper Virus Production," *Mol. Cell. Biol.* 6:2895–2902 (Aug., 1986).
Miller et al., "Construction and Properties of Retrovirus Packaging Cells Based on Gibbon Ape Leukemia Virus," *J. Virol.* 65:2220–2224 (May, 1991).
Gossen and Bujard, Tight Control of Gene Expression in Mammalian Cells by Tetracycline–Responsive Promoters, *Proc. Natl. Acad. Sci. USA* 89:5547–5551 (Jun., 1992).
Bunnell et al., "High–efficiency Retroviral–Mediated Gene Transfer into Human and Non Human Primate Peripheral Blood Lymphocytes," *Proc. Natl. Acad. Sci. USA* 92:7730–7743 (Aug., 1995).
Bauer Jr. et al., "Improved Transfer of the Leukocyte Integrin CD18 Subunit Into Hematopoietic Cell Lines by Using Retroviral Vectors Having a Gibbon Ape Leukemia Virus Envelope," *Blood* 86:2379–2387 (Sep. 15, 1995).
Cosset et al., "High–Titer Packaging Cells Producing Recombinant Retroviruses Resistant to Human Serum," *J. Virol.* 70:5701–5705 (Aug., 1996).
Naviaux et al., "The pCL Vector System: Rapid Production of Helper–Free, High–Titer, Recombinant Retroviruses," *J. Virol.* 70:5701–5705 (Aug., 1996).

*Primary Examiner*—Terry McKelvey
*Attorney, Agent, or Firm*—Townsend and Townsend and Crew LLP

[57] ABSTRACT

Retroviral packaging cells produce replication-defective retroviral particles capable of binding to *Mus dunni* endogenous virus retroviral receptors on target cells and are useful in gene transfer and gene therapy. The packaging cell employs a vector encoding a *M. dunni* retroviral Env protein and produces the retroviral particles at high titer.

12 Claims, No Drawings

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 8655 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

| | | | | | |
|---|---|---|---|---|---|
| GGTCGATCCT | CCTCTACACT | ATGCTTAGTG | CATGAGGTTC | GACCCCAGAG | CTCTGGTCTT | 60 |
| TGTGCTTTCT | TGTCGTGGCT | TCATTAAATC | TTACTCTCTA | TATTTGGTCT | AAGTGTCTTC | 120 |
| TTGGGTCCGC | GGCTGTCCCG | AGGCTTGAGT | GAGGAACTCC | CTGCGGGGAT | TCTTCATTTG | 180 |
| GTGCGTTGGC | CGGGAATCAG | CGCGACCACC | CAGAGGTCCT | AGGCCTACTT | AGAGGTAAGA | 240 |
| TTTTCTGTTC | TGTTTTGGTC | TGGTATCTGC | GTGCTGTTTC | TACGTTTGGT | GTCTGTATTC | 300 |
| TGTTTCTTCA | TTTGGTGCGA | TCGCAGTTTC | TGTTTTGCGG | ACGCTCGGTG | AGGCCGTGCT | 360 |
| TCGAGAGGGA | GCGCGGAGTG | GATAAGGACA | GACGTGTCCA | GGTGTCCACC | GTCCGTTCAC | 420 |
| CCTGGGAGAC | GTCCCAGGCG | GAATAGGGGA | GGACCAGGGA | CACCTGGTGG | ACCCCTCAGC | 480 |
| CTTTGGGAGT | GGATGTGGAA | TCCCACCCCA | TAAGGAAGGG | AGTGGATGTG | GAATCCCACC | 540 |
| CCGTAAGGAA | GGGAGTGGAT | GTGGAATCCC | ACCCCGTCAG | GAAGGGAGTC | GATGTGGAAT | 600 |
| CCGACCCCAT | CCATCTGAAT | CTTTAAGTTG | TCTGTGGTCG | ACGCGAAGTC | GCCGCCGGTT | 660 |
| TTGGTTTCTT | TTTTGTCTCA | GTCTCGTGTC | CGCTCTTGTT | GTGTCTGCTA | TTATTTTAGA | 720 |
| AATGGGACAA | TCTGTCTCCA | CTCCCCTTTC | TCTAACCCTG | GAGCATTGGA | AGGAGGTAAA | 780 |
| AATCAGAGCA | CACAATCAGT | CAGTGGAGGT | TAGGAAAGGC | CCATGGCAAA | CTTTTTGCGC | 840 |
| CTCCGAGTGG | CCAACGTTTG | GAGTGGGCTG | GCCACCGGAG | GGTGCTTTTG | ACTTGTCACT | 900 |
| GATCGCCGCC | GTCAGGCGAA | TTGTTTTTCA | GGAAGAAGGG | GGTCACCCTG | ATCAGATCCC | 960 |
| CTACATTGTG | ACCTGGCAGA | GTCTCGTCCA | GTTCCCACCT | TCGTGGGTCA | AGCCCTGGAC | 1020 |
| CCCAAATCCT | TCGAAACTGA | CGGTTGCAGT | TGCCCAGTCC | GATGCAGCTG | AGAAATCTGG | 1080 |
| TCCGTCAGCA | CCCCCCAAGA | TTTATCCAGA | GATTGACGAC | CTCCTCTGGA | TGGACTCCCA | 1140 |
| ACCTCCCCCT | TACCCCCTGC | CCCAGCAGCC | ACCTGCAGCA | GCCCCACCTG | TGGCAGCCCC | 1200 |
| TCAGCCGGAA | CCAACAGCAA | GCGGGCTCA | GGGACCGGCG | GGAGGGACTC | GGAGCCGCCG | 1260 |
| GGGTCGGAGC | CCTGCAGAGG | AAGGGGGGCC | AGATTCCACA | GTTGCCTTGC | CCCTTAGAGC | 1320 |
| TCATGTGGGA | GGGCCAACGC | CAGGACCTAA | TGATCTCATT | CCTTTACAGT | ACTGGCCTTT | 1380 |
| TTCTTCTTCT | GATTTATATA | ATTGGAAAAC | TAACCACCCT | CCCTTCTCAG | AAAACCCCTC | 1440 |
| TGGGCTTACT | GGGCTCCTTG | AATCACTTAT | GTTCTCTCAT | CAGCCCACTT | GGGATGATTG | 1500 |
| TCAGCAGCTT | TTGCAGGTTC | TCTTTACCAC | AGAGGAAAGG | GAAAGAATCC | TGATGGAGGC | 1560 |
| AAGAAAAAAC | GTTCTAGGAG | AGGACGGCAC | ACCCACTGCT | CTCCCTAACC | TCGTGGACGA | 1620 |
| GGCTTTCCCC | TTGAACCGCC | CCAACTGGGA | CTACAACACT | GCGGAAGGTA | GGGGACGCCT | 1680 |
| CCTTGTCTAC | CGTCGGACTC | TGGTGGCAGG | TCTCAGAGGA | GCCGCAAGAC | GGCCCACCAA | 1740 |
| TTTGGCTAAG | GTAAGAGAGG | TCTTGCAGGG | GCAGACTGAA | CCACCCTCAG | TCTTTCTGGA | 1800 |
| GCGTCTTATG | GAGGCGTATA | GGAGGTACAC | CCCTTTCGAT | CCCTCGTCAG | AGGGACAGAA | 1860 |
| AGCCGCTGTA | GCCATGGCCT | TCATTGGCCA | GTCTGCTCCC | GATATTAAGA | AAAAGCTACA | 1920 |
| GAGGCTGGAG | GGGCTCCAAG | ATTATACGCT | CCAAGATTTA | GTGAAGGAAG | CAGAGAAGGT | 1980 |
| TTATCACAAG | AGAGAAACAG | AAGAAGAGAG | GCAGGAGAGA | GAAAAGAAAG | AAGTAGAGGA | 2040 |
| GAGGGAAAAT | AGGCGAGATC | GCCGTCAGGA | GAGAAATTTG | AGTAAGATTC | TGGCCGCAGT | 2100 |
| TATAAATGAT | AGGCAGTCAG | AAAAAGGCAG | AACAGGATTC | CTGGGCAACA | GGGCAGTGAA | 2160 |
| ACCGCCAGGT | GGCAGAAAGA | CGCCGCTGGA | AAAAGACCAA | TGCGCCTTTT | GCAAAGAAAA | 2220 |
| AGGACACTGG | GCTAAAGACT | GCCCTAAGAA | AAGAAGGCAA | TTCAAGGTCC | TGACCCTAGA | 2280 |

```
AGACGATTAG GGAAGTCGGG GCTCAGACCC CCTCCCTGAG CCTAGGGTAA CTTTGTCTGT    2340

GGAGGGGACT CCCGTTAATT TCCTGATAGA TACTGGAGCA GAGCATTCGG TACTCACCAG    2400

CCCCCTGGGC AAACTAGGCT CTAAAAGGAC CATAGTGGTT GGAGCCACTG GGAGTAAACT    2460

TTACCCCTGG ACAACCAAAA GAGCCTTACA GATAGATAAA AACATGGTGA CCCACTCTTT    2520

CCTGGTGATA CCTGAGTGTC CTGCTCCCCT TCTGGGACGT GATCTGTTAA CAAAACTAAA    2580

GGCTCAAGTT CAATTTACTT CAGAAGGTCC ACAAGTAAGC TGGGGAAAAG CCCCCCTTGC    2640

TTGCCTTGTC CTCAGCACGG AAGAAGAGTA CCGGTTGCAT GAAGAGCAAC CCAAAGGTGC    2700

AGCCCCTTTA GACTGGGTAA CTGCGTTCCC CAATGTCTGG GCGGAACAAG CAGGGATGGG    2760

GTTGGCTAAA CAAGTGCCTC CAGTCGTGGT AGAACTTAAG GCTGATGCTA CCCCCATCTC    2820

AGTAAGACAA TACCCCATGA GCAAGGAAGC TAAGGAGGGC ATCCGACCTC ATATTCGGAG    2880

GCTGCTAGAC CAAGGAATTT TAGTGGCCTG TCAGTCCCCC TGGAACACTC CACTTTTGCC    2940

AGTACGAAAG CCAGGGACCA ATGATTATCG CCCGGTACAA GACCTCCGGG AAGTTAATAA    3000

AAGGGTCCTG GACATTCACC CTACAGTCCC GAACCCGTAC AACTTACTAA GCTCTCTCCC    3060

ACCCGAGAGA ACCTGGTATA CGGTCCTGGA TTTAAAAGAT GCCTTCTTTT GCCTGCGTCT    3120

GCACCCCAAG AGTCAACTTC TGTTTGCCTT TGAATGGAGA GACCCAGAGG GCGGACAGAC    3180

TGGTCAATTA ACCTGGACTA GACTACCACA GGGGTTCAAA AACTCCCCTA CCCTGTTTGA    3240

CGAAGCCCTC CATCGGGATT TAGCACCCTT TCGCGCTCAA AACCCCCAGC TTACCCTACT    3300

GCAGTACGTA GATGATCTTT TAATCGCAGC CGCCTCAAAA GAGCTATGTC AACAGGGGAC    3360

TGAGAGACTC CTCACAGAAC TGGGGAATTT GGGGTATCGA GTTTCGGCTA AAAAGGCACA    3420

AATTTGTCAA ACTGAGGTAA TCTACTTGGG GTATACTTTG CGAGGAGGTA AAAGATGGCT    3480

CACTGAAGCC CGGAAAAAGA CTGTCATGAT GATTCCACCG CCAACCACAC CACGGCAGGT    3540

ACGTGAGTTT CTGGGGACTG CTGGCTTTTG TAGACTCTGG ATTCCAGGCT TTGCGACCCT    3600

AGCAGCACCC CTATATCCCT TGACTAGGGA AGGAATTCCC TTTGAATGGA AAGAAGAACA    3660

CCAAAGAGCT TTTGAGGCTA TCAAATCGTC TCTAATGACT GCCCCTGCGC TAGCATTACC    3720

AGACTTGACT AAGTCCTTCG TCCTATATGT GGACGAGAGA GCGGGCATAG CCAGAGGGGT    3780

GCTGACACAA GCACTAGGAC CCTGGAAGAG ACCGGTAGCC TATCTGTCAA AAAAACTGGA    3840

TCCCGTTGCT AGTGGATGGC CCACATGTCT GAAAGCTATT GCAGCAGTAG CCCTGCTGAT    3900

CAAAGATGCT GATAAACTGA CAATGGGACA GCAGGTGACT GTCGTGGCCC CTCATGCCCT    3960

GGAGAGTATT GTGCGGCAGC CACCTGATAG ATGGATGACT AATGCCCGGA TGACACACTA    4020

TCAGAGTCTG CTGCTAAATG ACCGGGTAAC CTTTGCCCCC CCTGCCATTC TCAACCCAGC    4080

CACCCTCCTC CCTCTAACGA ATGATTCCGT CCCAGTACAT CGATGTGCAG ACATCCTGGC    4140

TGAAGAAATT GGGACCAGAA AAGACCTGAC TGACCAACCC TGGCCTGGAG CTCCTAGCTG    4200

GTACACGGAT GGCAGCAGTT TTCTGATTGA GGGAAAGCGA AGGGCTGGAG CTGCGGTGGT    4260

GGATGGAAAA AAGGTAATTT GGGCAAGTGC CTTGCCTGAA GGAACTTCGG CACAGAAGGC    4320

TGAACTCATA GCGCTTACAC AGGCCCTCCG AGAGGCCGAA GGTAAGATCA TTAATATTTA    4380

CACTGACAGC CGCTATGCTT TTGCTACTGC ACATATCCAT GGGGCCATCT ACAGGCAGCG    4440

AGGGTTATTG ACTTCAGCCG GTAAAGACAT CAAAAACAAA GAAGAAATTC TGGCCCTGTT    4500

AGAAGCCATA CATGCGCCCA AGAAGGTAGC CATCATCCAC TGTCCCGGTC ACCAGAAAGG    4560

AGAGGACTTA GTGGCCAAGG GCAACCGGAT GGCAGACTCA GTAGCAAAAC AGGTTGCTCA    4620
```

```
GGGGGCCATG ATCTTAACTG AAAAAGGAAA TCCGTCCAAA AGCCCTGAGG ATGAAAACTA      4680

TGATATAAAA GAACTATTTT GGACTAGTGA TCCCCTCCCA TACTTTTTCG AAGGAAAAAT      4740

AGACTTGACA CCCGAGGAAG GAATAAAATT TGTGAAAGGA CTACACCAGT TTACCCACCT      4800

GGGAGTTGAA AAAATGATGA GACTGATTAA AAAGTCCCGG TATCAAGTCC CTAACTTGAA      4860

GTCAGTGGCT CAAAAGATTA TAAACTCCTG CAAAGCGTGT GCATTCACTA ATGCAACTAA      4920

AACCTACAAA GAACCTGGAA AGAGACAACG GGGAGACCGT CCTGGAGTGT ATTGGGAGGT      4980

GGATTTTACT GAAGTTAAAC CCGGAATGTA TGGTAATAAG TATCTGTTAG TATTTGTAGA      5040

CACCTTTTCA GGATGGGTTG AAGCGTTCCC CACTAAAACT GAGACTGCCC AGATTGTGGC      5100

CAAGAAGATT TTTGAAGAAA TCCTGCCAAG ATATGGAGTA CCTAAGGTAA TCGGGTCCGA      5160

CAATGGACCA GCCTTTGTTG CCCAGGTAAG TCAGGGATTG GCCACTCAGT TGGGCATTGA      5220

TTGGAAATTA CATTGTGCTT ACCGCCCTCA AGCTCAGGA CAGGTAGAGA GGATGAATAG      5280

AACATTAAAG GAGACCTTGA CTAAATTGGC CATGGAGACC GGCGGGAAAG ACTGGGTGGC      5340

TCTCCTCCCC CTTGCGCTCT TCCGAGCCCG GAACACCCCC GGACGTTTTG GGCTCACTCC      5400

TTTTGAAGTT CTGTATGGGG GACCTCCCCC TTTAATAAAA GATGGTGGAA CATTGGTTCC      5460

CGATTCAGGC TCTGTCTTAC CCTCCTCTTT GCTTATTCAT TTAAAGGCCC TGAAAGTAAT      5520

TAGGACCCAA ATTTGGGACC AGCTAAAGAC GGCCTACACC CCAGGGACCA CCGCAGTACC      5580

CCACGAGTTC CAGGTCGGGG ACCAAGTCTT GGTCAGACGA CATCGAACCG GTAGCCTTGA      5640

ACCACGGTGG AAGGGACCCT ATTTAGTGTT ACTAACAACT CCTACGGCAG TGAAAGTTGA      5700

CGGGATTGCC TCCTGGATCC ACGCTTCACA CGTCAAGAGG GCCCCAGTC AAGATGAAGA      5760

AACCCACGAA GACAACTGGG CTGTGGAAGC CACTGATAAC CCTCTTAAGC TTCGCTTGCG      5820

TCGCAGGAGC CCCCTCCATC ACCCTGGACC TAGGGAACCA CAACCCTCAT GCCCCAGTTC      5880

AACAGTCTTG GGAAGTGCTT AATGAAAAGG GAGACGTTGT ATGGGTAGCC ACTGCAGTCC      5940

ATCCCCCTTG GACTTGGTGG CCTGATCTCA CACCTGACAT CTGTAAATTA GCAGCAGGAT      6000

CTCCCAATTG GGACCTTCCC GATCATACTG ACTTGAATAA CCCACCCTCT GAACAAAAGT      6060

GTGTCCCAAA CGGGGTAGGA AGCACTACTG GATGTTCGGG GCAGTTCTAT CGAGCTAATC      6120

TTAGGGCTGC ACAGTTTTAT GTTTGCCCTG GTCAGGGTCA GAAAGGAAAG CTGCAACAAG      6180

AATGTAGAGG GGCATCAGAC TACTTTTGCG GTAAATGGAC ATGTGAAACA CAGGGGAAG      6240

CCTACTGGAA GCCTTCCGCT GATTGGGACC TGATACGGT AAAACGTGGT AGTGGTTATG      6300

ATAAGCCAAA CCAAGGAGAA AGAAACCCAT ACAAATACCT AGATTCTGGG TGTGCTCTTA      6360

AAAATTACAG CCCCCCAGGA CCATGCAAAG GTAAATACTG CAACCCCCTA CTCATAAAAT      6420

TCACTGAGAA AGGGAAACAA GCTCGCCTGA GTTGGCTTAA AGGAAATAGG TGGGGTTGGC      6480

GAGTATATAT TCCAATAAGA GACCCTGGGT TTATCTTTAC GATTAGACTG ACAGTAAGAG      6540

ACCTGGCAGT AACATCCATA GGACCCAACA AGGTCCTTAC GGAACAGGCC CCCCAGTTG      6600

CACCGGCTCC CCCGAGAGTC CCAGCCGTGC CAGCTCCACC AACTTCACGG CCCTACACAG      6660

TAGGACCCTC ATTAGAGACA ACCTTAGCCT CCCCACCACT CCTAGATACA GAAAACCGTC      6720

TGGTCAGTCT AGTTCAGGGA GCCTTTTTAG TTTTAAATAG GACTAATCCT AATATGACTC      6780

AATCATGTTG GTTATGCTAT GCCTCTAACC CCCCTTATTA TGAAGGAATT GCTCAGACTA      6840

GAACTTACAA TATTACTTCA GATCATTCTC AATGTCTTTG GGGAGAGAAC AGGAAGTTGA      6900

CTCTGACAGC AGTTTCAGGA AATGGGCTTT GTTTAGGTCA GGTGCCCCAG GATAAATGGC      6960

ACCTCTGTAA CCAGACTCAA AATATCCGAC CTAACAAAGG TGGTCAGTAT CTAGTGCCTC      7020
```

```
CCATAGACAC AGTATGGGCT TGCAATACAG GTCTCACTCC TTGTATATCT ATGTCTGTTT      7080

TCAATAGCTC CAAAGATTTC TGTATTTTAG TTCAGCTTAT TCCTAGACTC CTGTATCATG      7140

ATGATAGCTC ATTTCTAGAC AAATTTGAAC ATCGGGTCCG CTGGAAAAGA GAACCCATTA      7200

CTTTAACGTT AGCAGTGCTT TTAGGATTGG GAGTGGCCGC AGCTGGGGTA GGTACTGGAA      7260

CCGCTGCCTT AATCCAGACC CCCCGATACT TTGAGGAATT ACGTACAGCT ATGGATACTG      7320

ATCTCAGAGC TATAGAACAC TCTATAACCA AACTAGAAGA ATCTTTAACT TCTCTGTCTG      7380

AGGTAGTACT GCAAAATAGG AGAGGATTAG ATTTGTTATT TCTTAAAGAA GGAGGACTTT      7440

GTGCTGCTCT CAAAGAGGAA TGTTGTTTCT ATGTCGACCA CTCGGGAGTG ATCAAAGATT      7500

CTATGGCCAA ACTTAGAGAA CGCCTAGATA TACGTCAAAG AGAGAGAGAG AGCAAACAAG      7560

GATGGTTTGA AAGCTGGTTT AATAAGTCCC CCTGGCTCAC CACTCTCCTT TCCACTATAG      7620

CGGGACCCTT GATTATACTT CTGCTTTTGC TTACTTTTGG CCCCTGCATT CTTAATAAGT      7680

TAGTAGCCTT TATTAGAGAA AGAATAAATG CAGTACAGGT TATGGTATTA AAACAACAAT      7740

ATCAGGTCTT CCAGGAGGCC GAAAACTCGC TCTAGGATTA GAGCTATTTA CAAGAAAAAA      7800

GGGGGGAATG AAGGGTTAAA GTAAAAATTA CTGACCACCT GAACTCTTCT TCACCCCAGA      7860

GTCCAACCCC TCCCATCTAG AAATTCTTCC TGAAACACTC CTAAACTCCT TAACATTCCT      7920

GAACTCTTCT TCACCCCAGA GTCCAACCCC TCCCATCTAG AAATTCTTCC TGAAACACTC      7980

CTAAACTCCT TAACATTCCT GAACTCTTCT TCACCCCAGA GTCCAACCCC TCCCATCTAG      8040

AAATTCTTCC TGAAACACTC CTAAACTCCT TAACATTCCT GAACTCTTCT TCACCCCAGA      8100

GTCCAACCCC TCCCATCTAG AAATTCTTCC TGAAACACTC CTAAACTCCT TAACATTCCT      8160

GAACTCTTCT TCACCCCAGA GTCCAACCCC TCCCATCTAG AAATTCTTCC TGAAACACTC      8220

CTAAACTCCT TAACATTCCT GAACTCTTCT TCACCCCAGA GTCCAACCCC TCCCATCTAG      8280

AAATTCTTCC TGAACCACTC CTAAACTCCT TAACATTCCT GAACTCTTCC TGAACCCATC      8340

ACCCCAAAGC ACGACCCCTC CCAGAAACAT TTTTAAGATA AAGGTTTCCT GGAACAACCT      8400

CAAGATGTTA CACAGCCCCC TTAATTACGC AGAACTCCCC TGGCAGAACA CCTTGACCTT      8460

TGGCAGAACT CTTTAATTGA GTAAAACCTG TACTTTCCCT ACCCTGCTTC CCCCCTCGGT      8520

TTTTGCCTAT ATAAGCCTGT AAGAACTTTA GCTCGAGGTC GATCCTCCTC TACACTATGC      8580

TTAGTGCATG AGGTTCGACC CCAGAGCTCT GGTCTTTGTG CTTTCTTGTC GTGGCTTCAT      8640

TAAATCTTAC TCTCT                                                      8655
```

(2) INFORMATION FOR SEQ ID NO:2:

(i) SEQUENCE CHARACTERISTICS:
        (A) LENGTH: 622 amino acids
        (B) TYPE: amino acid
        (D) TOPOLOGY: linear (ii) MOLECULE TYPE: peptide (xi) SEQUENCE DESCRIPTION: SEQ ID NO:2:

```
Met Gly Asp Val Pro Gly Gly Ile Gly Glu Asp Gln Gly His Leu Val
1               5                   10                  15

Asp Pro Ser Ala Phe Gly Ser Gly Cys Gly Ile Pro Pro His Lys Glu
            20                  25                  30

Gly Ser Gly Cys Gly Ile Pro Pro Arg Lys Glu Gly Ser Gly Cys Gly
        35                  40                  45

Ile Pro Pro Arg Gln Glu Gly Ser Arg Cys Gly Ile Arg Pro His Pro
```

-continued

```
            50                  55                  60
Ser Glu Ser Leu Ser Cys Leu Trp Ser Thr Arg Ser Arg Arg Phe
65                  70                  75                  80

Trp Phe Leu Phe Cys Leu Ser Leu Val Ser Ala Leu Val Val Ser Ala
                85                  90                  95

Ile Ile Leu Glu Met Gly Gln Ser Val Ser Thr Pro Leu Ser Leu Thr
                100                 105                 110

Leu Glu His Trp Lys Glu Val Lys Ile Arg Ala His Asn Gln Ser Val
                115                 120                 125

Glu Val Arg Lys Gly Pro Trp Gln Thr Phe Cys Ala Ser Glu Trp Pro
                130                 135                 140

Thr Phe Gly Val Gly Trp Pro Pro Glu Gly Ala Phe Asp Leu Ser Leu
145                 150                 155                 160

Ile Ala Ala Val Arg Arg Ile Val Phe Gln Glu Glu Gly Gly His Pro
                165                 170                 175

Asp Gln Ile Pro Tyr Ile Val Thr Trp Gln Ser Leu Val Gln Phe Pro
                180                 185                 190

Pro Ser Trp Val Lys Pro Trp Thr Pro Asn Pro Ser Lys Leu Thr Val
                195                 200                 205

Ala Val Ala Gln Ser Asp Ala Ala Glu Lys Ser Gly Pro Ser Ala Pro
                210                 215                 220

Pro Lys Ile Tyr Pro Glu Ile Asp Asp Leu Leu Trp Met Asp Ser Gln
225                 230                 235                 240

Pro Pro Pro Tyr Pro Leu Pro Gln Gln Pro Ala Ala Ala Pro Pro
                245                 250                 255

Val Ala Ala Pro Gln Pro Glu Pro Thr Ala Ser Gly Ala Gln Gly Pro
                260                 265                 270

Ala Gly Gly Thr Arg Ser Arg Arg Gly Arg Ser Pro Ala Glu Glu Gly
                275                 280                 285

Gly Pro Asp Ser Thr Val Ala Leu Pro Leu Arg Ala His Val Gly Gly
                290                 295                 300

Pro Thr Pro Gly Pro Asn Asp Leu Ile Pro Leu Gln Tyr Trp Pro Phe
305                 310                 315                 320

Ser Ser Ser Asp Leu Tyr Asn Trp Lys Thr Asn His Pro Pro Phe Ser
                325                 330                 335

Glu Asn Pro Ser Gly Leu Thr Gly Leu Leu Glu Ser Leu Met Phe Ser
                340                 345                 350

His Gln Pro Thr Trp Asp Asp Cys Gln Gln Leu Leu Gln Val Leu Phe
                355                 360                 365

Thr Thr Glu Glu Arg Glu Arg Ile Leu Met Glu Ala Arg Lys Asn Val
                370                 375                 380

Leu Gly Glu Asp Gly Thr Pro Thr Ala Leu Pro Asn Leu Val Asp Glu
385                 390                 395                 400

Ala Phe Pro Leu Asn Arg Pro Asn Trp Asp Tyr Asn Thr Ala Glu Gly
                405                 410                 415

Arg Gly Arg Leu Leu Val Tyr Arg Arg Thr Leu Val Ala Gly Leu Arg
                420                 425                 430

Gly Ala Ala Arg Arg Pro Thr Asn Leu Ala Lys Val Arg Glu Val Leu
                435                 440                 445

Gln Gly Gln Thr Glu Pro Pro Ser Val Phe Leu Glu Arg Leu Met Glu
                450                 455                 460

Ala Tyr Arg Arg Tyr Thr Pro Phe Asp Pro Ser Ser Glu Gly Gln Lys
465                 470                 475                 480
```

```
Ala Ala Val Ala Met Ala Phe Ile Gly Gln Ser Ala Pro Asp Ile Lys
                485                 490                 495

Lys Lys Leu Gln Arg Leu Glu Gly Leu Gln Asp Tyr Thr Leu Gln Asp
            500                 505                 510

Leu Val Lys Glu Ala Glu Lys Val Tyr His Lys Arg Glu Thr Glu Glu
        515                 520                 525

Glu Arg Gln Glu Arg Glu Lys Lys Glu Val Glu Arg Glu Asn Arg
    530                 535                 540

Arg Asp Arg Arg Gln Glu Arg Asn Leu Ser Lys Ile Leu Ala Ala Val
545                 550                 555                 560

Ile Asn Asp Arg Gln Ser Glu Lys Gly Arg Thr Gly Phe Leu Gly Asn
                565                 570                 575

Arg Ala Val Lys Pro Gly Gly Arg Lys Thr Pro Leu Glu Lys Asp
            580                 585                 590

Gln Cys Ala Phe Cys Lys Glu Lys Gly His Trp Ala Lys Asp Cys Pro
        595                 600                 605

Lys Lys Arg Arg Gln Phe Lys Val Leu Thr Leu Glu Asp Asp
    610                 615                 620

(2) INFORMATION FOR SEQ ID NO:3:

(i) SEQUENCE CHARACTERISTICS:
        (A) LENGTH: 522 amino acids
        (B) TYPE: amino acid
        (D) TOPOLOGY: linear (ii) MOLECULE TYPE: peptide (xi) SEQUENCE DESCRIPTION: SEQ ID NO:3:

Met Gly Gln Ser Val Ser Thr Pro Leu Ser Leu Thr Leu Glu His Trp
1               5                   10                  15

Lys Glu Val Lys Ile Arg Ala His Asn Gln Ser Val Glu Val Arg Lys
            20                  25                  30

Gly Pro Trp Gln Thr Phe Cys Ala Ser Glu Trp Pro Thr Phe Gly Val
        35                  40                  45

Gly Trp Pro Pro Glu Gly Ala Phe Asp Leu Ser Leu Ile Ala Ala Val
    50                  55                  60

Arg Arg Ile Val Phe Gln Glu Gly Gly His Pro Asp Gln Ile Pro
65                  70                  75                  80

Tyr Ile Val Thr Trp Gln Ser Leu Val Gln Phe Pro Pro Ser Trp Val
                85                  90                  95

Lys Pro Trp Thr Pro Asn Pro Ser Lys Leu Thr Val Ala Val Ala Gln
            100                 105                 110

Ser Asp Ala Ala Glu Lys Ser Gly Pro Ser Ala Pro Lys Ile Tyr
        115                 120                 125

Pro Glu Ile Asp Asp Leu Leu Trp Met Asp Ser Gln Pro Pro Tyr
    130                 135                 140

Pro Leu Pro Gln Gln Pro Pro Ala Ala Ala Pro Val Ala Ala Pro
145                 150                 155                 160

Gln Pro Glu Pro Thr Ala Ser Gly Ala Gln Gly Pro Ala Gly Gly Thr
                165                 170                 175

Arg Ser Arg Arg Gly Arg Ser Pro Ala Glu Glu Gly Pro Asp Ser
            180                 185                 190

Thr Val Ala Leu Pro Leu Arg Ala His Val Gly Gly Pro Thr Pro Gly
        195                 200                 205
```

```
Pro Asn Asp Leu Ile Pro Leu Gln Tyr Trp Pro Phe Ser Ser Ser Asp
    210                 215                 220

Leu Tyr Asn Trp Lys Thr Asn His Pro Pro Phe Ser Glu Asn Pro Ser
225                 230                 235                 240

Gly Leu Thr Gly Leu Leu Glu Ser Leu Met Phe Ser His Gln Pro Thr
                245                 250                 255

Trp Asp Asp Cys Gln Gln Leu Leu Gln Val Leu Phe Thr Thr Glu Glu
                260                 265                 270

Arg Glu Arg Ile Leu Met Glu Ala Arg Lys Asn Val Leu Gly Glu Asp
            275                 280                 285

Gly Thr Pro Thr Ala Leu Pro Asn Leu Val Asp Glu Ala Phe Pro Leu
290                 295                 300

Asn Arg Pro Asn Trp Asp Tyr Asn Thr Ala Glu Gly Arg Gly Arg Leu
305                 310                 315                 320

Leu Val Tyr Arg Arg Thr Leu Val Ala Gly Leu Arg Gly Ala Ala Arg
                325                 330                 335

Arg Pro Thr Asn Leu Ala Lys Val Arg Glu Val Leu Gln Gly Gln Thr
                340                 345                 350

Glu Pro Pro Ser Val Phe Leu Glu Arg Leu Met Glu Ala Tyr Arg Arg
            355                 360                 365

Tyr Thr Pro Phe Asp Pro Ser Ser Glu Gly Gln Lys Ala Ala Val Ala
370                 375                 380

Met Ala Phe Ile Gly Gln Ser Ala Pro Asp Ile Lys Lys Lys Leu Gln
385                 390                 395                 400

Arg Leu Glu Gly Leu Gln Asp Tyr Thr Leu Gln Asp Leu Val Lys Glu
                405                 410                 415

Ala Glu Lys Val Tyr His Lys Arg Glu Thr Glu Glu Glu Arg Gln Glu
                420                 425                 430

Arg Glu Lys Lys Glu Val Glu Glu Arg Glu Asn Arg Arg Asp Arg Arg
            435                 440                 445

Gln Glu Arg Asn Leu Ser Lys Ile Leu Ala Ala Val Ile Asn Asp Arg
450                 455                 460

Gln Ser Glu Lys Gly Arg Thr Gly Phe Leu Gly Asn Arg Ala Val Lys
465                 470                 475                 480

Pro Pro Gly Gly Arg Lys Thr Pro Leu Glu Lys Asp Gln Cys Ala Phe
                485                 490                 495

Cys Lys Glu Lys Gly His Trp Ala Lys Asp Cys Pro Lys Lys Arg Arg
                500                 505                 510

Gln Phe Lys Val Leu Thr Leu Glu Asp Asp
            515                 520

(2) INFORMATION FOR SEQ ID NO:4:

(i) SEQUENCE CHARACTERISTICS:
        (A) LENGTH: 1203 amino acids
        (B) TYPE: amino acid
        (D) TOPOLOGY: linear (ii) MOLECULE TYPE: peptide (xi) SEQUENCE DESCRIPTION: SEQ ID NO:4:

Gly Ser Arg Gly Ser Asp Pro Leu Pro Glu Pro Arg Val Thr Leu Ser
1               5                   10                  15

Val Glu Gly Thr Pro Val Asn Phe Leu Ile Asp Thr Gly Ala Glu His
                20                  25                  30

Ser Val Leu Thr Ser Pro Leu Gly Lys Leu Gly Ser Lys Arg Thr Ile
```

```
                  35                  40                  45
Val Val Gly Ala Thr Gly Ser Lys Leu Tyr Pro Trp Thr Thr Lys Arg
     50                  55                  60

Ala Leu Gln Ile Asp Lys Asn Met Val Thr His Ser Phe Leu Val Ile
 65                  70                  75                  80

Pro Glu Cys Pro Ala Pro Leu Leu Gly Arg Asp Leu Leu Thr Lys Leu
                 85                  90                  95

Lys Ala Gln Val Gln Phe Thr Ser Glu Gly Pro Gln Val Ser Trp Gly
                100                 105                 110

Lys Ala Pro Leu Ala Cys Leu Val Leu Ser Thr Glu Glu Tyr Arg
                115                 120                 125

Leu His Glu Glu Gln Pro Lys Gly Ala Ala Pro Leu Asp Trp Val Thr
                130                 135                 140

Ala Phe Pro Asn Val Trp Ala Glu Gln Ala Gly Met Gly Leu Ala Lys
145                 150                 155                 160

Gln Val Pro Pro Val Val Glu Leu Lys Ala Asp Ala Thr Pro Ile
                    165                 170                 175

Ser Val Arg Gln Tyr Pro Met Ser Lys Glu Ala Lys Glu Gly Ile Arg
                180                 185                 190

Pro His Ile Arg Arg Leu Leu Asp Gln Gly Ile Leu Val Ala Cys Gln
                195                 200                 205

Ser Pro Trp Asn Thr Pro Leu Leu Pro Val Arg Lys Pro Gly Thr Asn
210                 215                 220

Asp Tyr Arg Pro Val Gln Asp Leu Arg Glu Val Asn Lys Arg Val Leu
225                 230                 235                 240

Asp Ile His Pro Thr Val Pro Asn Pro Tyr Asn Leu Leu Ser Ser Leu
                    245                 250                 255

Pro Pro Glu Arg Thr Trp Tyr Thr Val Leu Asp Leu Lys Asp Ala Phe
                260                 265                 270

Phe Cys Leu Arg Leu His Pro Lys Ser Gln Leu Leu Phe Ala Phe Glu
                275                 280                 285

Trp Arg Asp Pro Glu Gly Gly Gln Thr Gly Gln Leu Thr Trp Thr Arg
                290                 295                 300

Leu Pro Gln Gly Phe Lys Asn Ser Pro Thr Leu Phe Asp Glu Ala Leu
305                 310                 315                 320

His Arg Asp Leu Ala Pro Phe Arg Ala Gln Asn Pro Gln Leu Thr Leu
                    325                 330                 335

Leu Gln Tyr Val Asp Asp Leu Leu Ile Ala Ala Ser Lys Glu Leu
                340                 345                 350

Cys Gln Gln Gly Thr Glu Arg Leu Leu Thr Glu Leu Gly Asn Leu Gly
                355                 360                 365

Tyr Arg Val Ser Ala Lys Lys Ala Gln Ile Cys Gln Thr Glu Val Ile
                370                 375                 380

Tyr Leu Gly Tyr Thr Leu Arg Gly Gly Lys Arg Trp Leu Thr Glu Ala
385                 390                 395                 400

Arg Lys Lys Thr Val Met Met Ile Pro Pro Thr Thr Pro Arg Gln
                    405                 410                 415

Val Arg Glu Phe Leu Gly Thr Ala Gly Phe Cys Arg Leu Trp Ile Pro
                420                 425                 430

Gly Phe Ala Thr Leu Ala Ala Pro Leu Tyr Pro Leu Thr Arg Glu Gly
                435                 440                 445

Ile Pro Phe Glu Trp Lys Glu Glu His Gln Arg Ala Phe Glu Ala Ile
                450                 455                 460
```

-continued

```
Lys Ser Ser Leu Met Thr Ala Pro Ala Leu Ala Leu Pro Asp Leu Thr
465                 470                 475                 480

Lys Ser Phe Val Leu Tyr Val Asp Glu Arg Ala Gly Ile Ala Arg Gly
                485                 490                 495

Val Leu Thr Gln Ala Leu Gly Pro Trp Lys Arg Pro Val Ala Tyr Leu
            500                 505                 510

Ser Lys Lys Leu Asp Pro Val Ala Ser Gly Trp Pro Thr Cys Leu Lys
        515                 520                 525

Ala Ile Ala Ala Val Ala Leu Leu Ile Lys Asp Ala Asp Lys Leu Thr
    530                 535                 540

Met Gly Gln Gln Val Thr Val Ala Pro His Ala Leu Glu Ser Ile
545                 550                 555                 560

Val Arg Gln Pro Pro Asp Arg Trp Met Thr Asn Ala Arg Met Thr His
                565                 570                 575

Tyr Gln Ser Leu Leu Asn Asp Arg Val Thr Phe Ala Pro Pro Ala
            580                 585                 590

Ile Leu Asn Pro Ala Thr Leu Leu Pro Leu Thr Asn Asp Ser Val Pro
        595                 600                 605

Val His Arg Cys Ala Asp Ile Leu Ala Glu Ile Gly Thr Arg Lys
    610                 615                 620

Asp Leu Thr Asp Gln Pro Trp Pro Gly Ala Pro Ser Trp Tyr Thr Asp
625                 630                 635                 640

Gly Ser Ser Phe Leu Ile Glu Gly Lys Arg Arg Ala Gly Ala Ala Val
                645                 650                 655

Val Asp Gly Lys Lys Val Ile Trp Ala Ser Ala Leu Pro Glu Gly Thr
            660                 665                 670

Ser Ala Gln Lys Ala Glu Leu Ile Ala Leu Thr Gln Ala Leu Arg Glu
        675                 680                 685

Ala Glu Gly Lys Ile Ile Asn Ile Tyr Thr Asp Ser Arg Tyr Ala Phe
    690                 695                 700

Ala Thr Ala His Ile His Gly Ala Ile Tyr Arg Gln Arg Gly Leu Leu
705                 710                 715                 720

Thr Ser Ala Gly Lys Asp Ile Lys Asn Lys Glu Glu Ile Leu Ala Leu
                725                 730                 735

Leu Glu Ala Ile His Ala Pro Lys Lys Val Ala Ile Ile His Cys Pro
            740                 745                 750

Gly His Gln Lys Gly Glu Asp Leu Val Ala Lys Gly Asn Arg Met Ala
        755                 760                 765

Asp Ser Val Ala Lys Gln Val Ala Gln Gly Ala Met Ile Leu Thr Glu
    770                 775                 780

Lys Gly Asn Pro Ser Lys Ser Pro Glu Asp Glu Asn Tyr Asp Ile Lys
785                 790                 795                 800

Glu Leu Phe Trp Thr Ser Asp Pro Leu Pro Tyr Phe Phe Glu Gly Lys
                805                 810                 815

Ile Asp Leu Thr Pro Glu Glu Gly Ile Lys Phe Val Lys Gly Leu His
            820                 825                 830

Gln Phe Thr His Leu Gly Val Glu Lys Met Met Arg Leu Ile Lys Lys
        835                 840                 845

Ser Arg Tyr Gln Val Pro Asn Leu Lys Ser Val Ala Gln Lys Ile Ile
    850                 855                 860

Asn Ser Cys Lys Ala Cys Ala Phe Thr Asn Ala Thr Lys Thr Tyr Lys
865                 870                 875                 880
```

```
Glu Pro Gly Lys Arg Gln Arg Gly Asp Arg Pro Gly Val Tyr Trp Glu
                885                 890                 895

Val Asp Phe Thr Glu Val Lys Pro Gly Met Tyr Gly Asn Lys Tyr Leu
            900                 905                 910

Leu Val Phe Val Asp Thr Phe Ser Gly Trp Val Glu Ala Phe Pro Thr
            915                 920                 925

Lys Thr Glu Thr Ala Gln Ile Val Ala Lys Lys Ile Phe Glu Glu Ile
    930                 935                 940

Leu Pro Arg Tyr Gly Val Pro Lys Val Ile Gly Ser Asp Asn Gly Pro
945                 950                 955                 960

Ala Phe Val Ala Gln Val Ser Gln Gly Leu Ala Thr Gln Leu Gly Ile
                965                 970                 975

Asp Trp Lys Leu His Cys Ala Tyr Arg Pro Gln Ser Ser Gly Gln Val
            980                 985                 990

Glu Arg Met Asn Arg Thr Leu Lys Glu Thr Leu Thr Lys Leu Ala Met
            995                 1000                1005

Glu Thr Gly Gly Lys Asp Trp Val Ala Leu Leu Pro Leu Ala Leu Phe
    1010                1015                1020

Arg Ala Arg Asn Thr Pro Gly Arg Phe Gly Leu Thr Pro Phe Glu Val
1025                1030                1035                1040

Leu Tyr Gly Gly Pro Pro Leu Ile Lys Asp Gly Tyr Gly Thr Leu Val
                1045                1050                1055

Pro Asp Ser Gly Ser Val Leu Pro Ser Ser Leu Leu Ile His Leu Lys
            1060                1065                1070

Ala Leu Lys Val Ile Arg Thr Gln Ile Trp Asp Gln Leu Lys Thr Ala
            1075                1080                1085

Tyr Thr Pro Gly Thr Thr Ala Val Pro His Glu Phe Gln Val Gly Asp
    1090                1095                1100

Gln Val Leu Val Arg Arg His Arg Thr Gly Ser Leu Glu Pro Arg Trp
1105                1110                1115                1120

Lys Gly Pro Tyr Leu Val Leu Leu Thr Thr Pro Thr Ala Val Lys Val
                1125                1130                1135

Asp Gly Ile Ala Ser Trp Ile His Ala Ser His Val Lys Arg Ala Pro
            1140                1145                1150

Ser Gln Asp Glu Glu Thr His Glu Asp Asn Trp Ala Val Glu Ala Thr
            1155                1160                1165

Asp Asn Pro Leu Lys Leu Arg Leu Leu Arg Arg Ser Pro Leu His His
    1170                1175                1180

Pro Gly Pro Arg Glu Pro Gln Pro Ser Cys Pro Ile Ser Thr Val Leu
1185                1190                1195                1200

Gly Ser Ala (2) INFORMATION FOR SEQ ID NO:5:

(i) SEQUENCE CHARACTERISTICS:
        (A) LENGTH: 673 amino acids
        (B) TYPE: amino acid
        (D) TOPOLOGY: linear (ii) MOLECULE TYPE: peptide (xi) SEQUENCE DESCRIPTION: SEQ ID NO:5:

Met Lys Lys Pro Thr Lys Thr Thr Gly Leu Trp Lys Pro Leu Ile Thr
    1               5                   10                  15

Leu Leu Ser Phe Ala Cys Val Ala Gly Ala Pro Ser Ile Thr Leu Asp
                20                  25                  30
```

```
Leu Gly Asn His Asn Pro His Ala Pro Val Gln Gln Ser Trp Glu Val
         35                  40                  45
Leu Asn Glu Lys Gly Asp Val Val Trp Val Ala Thr Ala Val His Pro
     50                  55                  60
Pro Trp Thr Trp Trp Pro Asp Leu Thr Pro Asp Ile Cys Lys Leu Ala
 65                  70                  75                  80
Ala Gly Ser Pro Asn Trp Asp Leu Pro Asp His Thr Asp Leu Asn Asn
                 85                  90                  95
Pro Pro Ser Glu Gln Lys Cys Val Pro Asn Gly Val Gly Ser Thr Thr
            100                 105                 110
Gly Cys Ser Gly Gln Phe Tyr Arg Ala Asn Leu Arg Ala Ala Gln Phe
        115                 120                 125
Tyr Val Cys Pro Gly Gln Gly Gln Lys Gly Lys Leu Gln Gln Glu Cys
    130                 135                 140
Arg Gly Ala Ser Asp Tyr Phe Cys Gly Lys Trp Thr Cys Glu Thr Thr
145                 150                 155                 160
Gly Glu Ala Tyr Trp Lys Pro Ser Ala Asp Trp Asp Leu Ile Thr Val
                165                 170                 175
Lys Arg Gly Ser Gly Tyr Asp Lys Pro Asn Gln Gly Glu Arg Asn Pro
            180                 185                 190
Tyr Lys Tyr Leu Asp Ser Gly Cys Ala Leu Lys Asn Tyr Ser Pro Pro
        195                 200                 205
Gly Pro Cys Lys Gly Lys Tyr Cys Asn Pro Leu Leu Ile Lys Phe Thr
    210                 215                 220
Glu Lys Gly Lys Gln Ala Arg Leu Ser Trp Leu Lys Gly Asn Arg Trp
225                 230                 235                 240
Gly Trp Arg Val Tyr Ile Pro Ile Arg Asp Pro Gly Phe Ile Phe Thr
                245                 250                 255
Ile Arg Leu Thr Val Arg Asp Leu Ala Val Thr Ser Ile Gly Pro Asn
            260                 265                 270
Lys Val Leu Thr Glu Gln Ala Pro Pro Val Ala Pro Ala Pro Pro Arg
        275                 280                 285
Val Pro Ala Val Pro Ala Pro Thr Ser Arg Pro Tyr Thr Val Gly
    290                 295                 300
Pro Ser Leu Glu Thr Thr Leu Ala Ser Pro Pro Leu Leu Asp Thr Glu
305                 310                 315                 320
Asn Arg Leu Val Ser Leu Val Gln Gly Ala Phe Leu Val Leu Asn Arg
                325                 330                 335
Thr Asn Pro Asn Met Thr Gln Ser Cys Trp Leu Cys Tyr Ala Ser Asn
            340                 345                 350
Pro Pro Tyr Tyr Glu Gly Ile Ala Gln Thr Arg Thr Tyr Asn Ile Thr
        355                 360                 365
Ser Asp His Ser Gln Cys Leu Trp Gly Glu Asn Arg Lys Leu Thr Leu
    370                 375                 380
Thr Ala Val Ser Gly Asn Gly Leu Cys Leu Gly Gln Val Pro Gln Asp
385                 390                 395                 400
Lys Trp His Leu Cys Asn Gln Thr Gln Asn Ile Arg Pro Asn Lys Gly
                405                 410                 415
Gly Gln Tyr Leu Val Pro Pro Ile Asp Thr Val Trp Ala Cys Asn Thr
            420                 425                 430
Gly Leu Thr Pro Cys Ile Ser Met Ser Val Phe Asn Ser Ser Lys Asp
        435                 440                 445
```

```
Phe Cys Ile Leu Val Gln Leu Ile Pro Arg Leu Leu Tyr His Asp Asp
    450                 455                 460

Ser Ser Phe Leu Asp Lys Phe Glu His Arg Val Arg Trp Lys Arg Glu
465                 470                 475                 480

Pro Ile Thr Leu Thr Leu Ala Val Leu Leu Gly Leu Gly Val Ala Ala
                    485                 490                 495

Ala Gly Val Gly Thr Gly Thr Ala Ala Leu Ile Gln Thr Pro Arg Tyr
                500                 505                 510

Phe Glu Glu Leu Arg Thr Ala Met Asp Thr Asp Leu Arg Ala Ile Glu
            515                 520                 525

His Ser Ile Thr Lys Leu Glu Glu Ser Leu Thr Ser Leu Ser Glu Val
    530                 535                 540

Val Leu Gln Asn Arg Arg Gly Leu Asp Leu Leu Phe Leu Lys Glu Gly
545                 550                 555                 560

Gly Leu Cys Ala Ala Leu Lys Glu Glu Cys Cys Phe Tyr Val Asp His
                565                 570                 575

Ser Gly Val Ile Lys Asp Ser Met Ala Lys Leu Arg Glu Arg Leu Asp
                580                 585                 590

Ile Arg Gln Arg Glu Arg Glu Ser Lys Gln Gly Trp Phe Glu Ser Trp
            595                 600                 605

Phe Asn Lys Ser Pro Trp Leu Thr Thr Leu Leu Ser Thr Ile Ala Gly
    610                 615                 620

Pro Leu Ile Ile Leu Leu Leu Leu Thr Phe Gly Pro Cys Ile Leu
625                 630                 635                 640

Asn Lys Leu Val Ala Phe Ile Arg Glu Arg Ile Asn Ala Val Gln Val
                645                 650                 655

Met Val Leu Lys Gln Gln Tyr Gln Val Phe Gln Glu Ala Glu Asn Ser
                660                 665                 670

Leu (2) INFORMATION FOR SEQ ID NO:6:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:6:

TTGGTGGCCT GATCTCACAC CTG                                            23

(2) INFORMATION FOR SEQ ID NO:7:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:7:

CTCTCCTATT TTGCAGTACT ACCTC                                          25

(2) INFORMATION FOR SEQ ID NO:8:

(i) SEQUENCE CHARACTERISTICS:
          (A) LENGTH: 32 base pairs
```

```
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

CAGGGTCAGA AAGGAAAGCT GCAACAAGAA TG                              32

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CATTCTTGTT GCAGCTTTCC TTTCTGACCC TG                              32

(2) INFORMATION FOR SEQ ID NO:10:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GCCCACCGTG TGCCACCATG AAGAAACCCA CGAAGACAAC                      40

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GCGGTTAACA TAGCTCTAAT CCTAGAGCGA G                               31
```

*MUS DUNNI* ENDOGENOUS RETROVIRAL PACKAGING CELL LINES

RELATED APPLICATIONS

The present application claims the benefit U.S. Provisional Ser. No. 60/046,140, filed May 9, 1997, which is incorporated herein by reference.

GOVERNMENT SUPPORT

This work was supported by grants DK47754, HL54881 and HL36444 from the National Institutes of Health. The U.S. Government may have certain rights in the invention.

BACKGROUND OF THE INVENTION

Retroviral vectors promote the transfer of genes into a variety of cell types from many animal species. Retroviral vectors are among the primary vehicles used for gene transfer into human somatic cells because of their ability to transfer genes efficiently into cells that are difficult to transfect by other methods.

A critical element in the production of the components to carry out retroviral mediated gene transfer is the cell that generates the retroviral particles carrying the gene to be transferred. These cells are called "packaging cells" because they "package" the retroviral vector which carries the gene of interest into a delivery vehicle, the retroviral particles. Packaging cell lines are designed to synthesize all retroviral proteins required for assembly of high-titer infectious virus, but should not produce any replication-competent virus. Thus, the retroviral vector consists of DNA sequences intended for transfer flanked by signals present at the ends of the retroviral genome, and the packaging cells are designed to produce all of the retroviral proteins and promote "packaging" of the retroviral RNA into virions. Retroviral vectors produced by using packaging cells can thus infect cells but cannot replicate further.

Retrovirus packaging cells provide useful tools for a variety of gene transfer applications. However, not all cell types can be efficiently infected by using the available packaging cell lines. The range of cells that are infectable by a retroviral particle is primarily determined by the envelope proteins of the virus and the presence of appropriate receptors for this protein on the surface of target cells. For example, viruses that infect human cells can be separated into eight groups based on the use of different receptors for cell entry.

Recent improvements include the design of packaging cells to produce vectors having a vesicular stomatitis virus G protein coat for expanded host range (Burns et al., *Proc. Natl. Acad. Sci. U.S.A.* 90:8033–8037 (1993); Lin et al., *Science* 265:666–669 (1994)), vectors that are resistant to human serum (Cosset et al., (1995)), and vectors that target to new cell-surface proteins (Kasahara et al., *Science* 1373–1376 (1994); Somia et al., *Proc. Natl. Acad. Sci. U.S.A.* 92:7570–7574 (1995)). However, there is still room for improvement to increase the efficiency and range of cell types that can be transduced using existing retroviral vectors. For example, treatment of genetic and acquired disease in humans would be greatly facilitated by the ability to transfer genes into hematopoietic stem cells, but transduction of these cells in large animals and humans remains low.

Packaging cells which produce amphotropic retrovirus (retroviruses which can infect cells from many species) were developed over ten years ago and are still commonly used because of the wide range of cell types from different species, including humans, that these vectors can transduce. (Cone et al., *Proc. Natl. Acad. Sci. U.S.A.* 81:6349–6353 (1984); Miller et al., *Mol. Cell. Biol.* 6:2895–2902 (1986); Miller et al., *Mol. Cell. Biol.* 5:431–437 (1985); and Sorge et al., *Mol. Cell. Biol.* 4:1730–1737 (1984)). More recently, packaging cells have been developed based on gibbon ape leukemia virus (GALV) (Miller et al., *J. Virol.* 65:2220–2224 (1991)) that produce vectors that use a different receptor than the prior known amphotrophic retroviruses for cell entry, and are capable of transducing myeloid, lymphoid, and airway epithelial cells at higher rates than amphotropic vectors do (Bauer et al., *Blood* 86:2379–2387 (1995); Bayle et al., *Hum. Gene Ther.* 4:161–170; Bunnell et al., *Proc. Natl. Acad. Sci. U.S.A.* 92:7739–7743 (1995); von Kalle et al., *Blood* 84:2890–2897).

The GALV and amphotropic retrovirus receptors are related phosphate transport proteins that exhibit wide, but different, patterns of tissue specific expression (Kavanaugh et al., *Proc. Natl. Acad. Sci. U.S.A.* 91:7071–7075 (1994)). The GALV receptor Glvr-1 (Pit-1) is most highly expressed in bone marrow, while the amphotropic receptor Ram-1 (Pit-2) is most highly expressed in the heart. It has been shown that 10A1 murine leukemia virus can use either mouse or human Glvr-1 or rat or human Ram-1 for cell entry (Miller et al., *J. Virol.* 68:8270–8276 (1994)).

What is needed in the art is a retroviral packaging system that offers advantages over currently available viral packaging systems and that is useful in a wide variety of gene transfer applications. The present invention addresses this and other related needs.

SUMMARY OF THE INVENTION

In one aspect the invention provides a cultured packaging cell for producing a replication-defective retroviral vector particle. The packaging cell is a vertebrate cell capable of expressing and assembling retroviral proteins, and comprises a vector encoding a retroviral envelope protein having amino acid residues of the *Mus dunni* endogenous virus (MDEV) or fragment thereof, that direct binding of the retroviral particle to the MDEV retroviral receptors on a target cell. The packaging cell further comprises a vector encoding retroviral Gag and Pol proteins, such that upon expression of the vectors in the presence of a vector having a sequence of a heterologous gene of interest, a replication-defective retroviral vector article is produced that binds to the MDEV retroviral receptors of target cells. The retrovirus gag and pol genes can be from, for example, Moloney murine leukemia virus. The cultured packaging cell can be an avian or mammalian cell capable of expressing and assembling retroviral proteins. The vectors encoding the retroviral Env protein, the retroviral Gag and Pol proteins, and the vector comprising a heterologous gene of interest can be integrated in a chromosome of the packaging cell.

In another aspect the invention provides a method for producing a replication-defective retroviral vector particle comprising a heterologous gene of interest. The method comprises transducing or transfecting a retroviral packaging cell with (a) a replication defective virus particle which comprises virus RNA transcribed from a recombinant DNA provirus, the provirus comprising virus long terminal repeat sequences (LTRs), a retrovirus packaging sequence, and a heterologous gene, or (b) a vector comprising the provirus. The packaging cell can be a vertebrate cell capable of expressing and assembling retroviral proteins and having (i) an integrated vector encoding a retroviral envelope protein having amino acid residues of the *Mus dunni* endogenous virus (MDEV) that direct binding of the retroviral particle to the MDEV retroviral receptors on a target cell, and (ii) an integrated vector encoding retroviral Gag and Pol proteins. The sequences which encode the retroviral Env protein, the retroviral Gag and Pol proteins, and the vector comprising the heterologous gene of interest are expressed, producing a replication-defective retroviral vector particle that binds to MDEV retroviral receptors of target cells.

In still another aspect of the present invention, methods are provided for transiently producing a replication-defective retroviral vector particle comprising a heterologous gene of interest. The method comprises transforming a transfecting vertebrate cell capable of expressing and assembling retroviral proteins with (i) a first vector comprising a retroviral gag gene; (ii) a second vector comprising a retroviral pol gene; (iii) a third vector comprising a *Mus dunni* endogenous virus env gene or a fragment thereof; and (iv) a (a) replication-defective virus particle which comprises virus RNA transcribed from a recombinant DNA provirus, the provirus comprising a virus long terminal repeat sequences (LTRs), a retrovirus packaging sequence, and a heterologous gene, or (b) a vector comprising the provirus. The transfected or transformed cell is capable of transiently expressing the protein encoded by the *M. dunni* endogenous virus env gene, the retrovirus gag and pol genes, and the product of the heterologous gene of interest. When expressed, a replication-defective retroviral vector particle is transiently produced which combined to *Mus dunni* endogenous virus receptor of target cells. In an alternative method, the retrovirus pol gene can be combined on a single vector.

In another aspect the invention provides a replication-defective retroviral vector particle containing the heterologous gene of interest produced by these methods.

DESCRIPTION OF THE SPECIFIC EMBODIMENTS

The present invention provides retrovirus packaging cell lines based on the *Mus dunni* endogenous virus (MDEV) class of retrovirus. MDEV packaging cells produce vectors capable of using a MDEV receptor for cell entry. The *Mus dunni* endogenous virus is capable of infecting a variety of cell types across a wide host range including mouse, rat, hamster, quail, cat, dog, baboon and human. Thus, the MDEV receptor is present on a variety of cells rendering MDEV pseudotype packaging cells useful in methods of mammalian and particularly human gene transfer.

The MDEV packaging cells are a stable and reproducible source of retroviral particles. Clones may be isolated from these populations that produce high titer virus. The packaging cell lines of the invention can be selected and cloned for other desirable properties, such as stability of in vivo growth, lack of production of helper virus, lack of reinfection by viral particles packaged in the cell, stability from genetic rearrangement and recombinational events, resistance to complement lysis, and improved ability to infect cells from higher mammals. The replication defective virus vectors produced by the MDEV packaging cell lines of the present invention permit the transfer of a wide variety of heterologous nucleic acid segments.

The packaging cell line is transduced or transfected with a replication defective virus vector, or a DNA construct having a strand corresponding to or complementary to a replication defective viral vector, containing the heterologous gene(s) of interest. Representative genes useful in the present invention include, among others, those which encode, for example, blood clotting factors, adenosine deaminase, interleukins, interferons, GM-CSF, G-CSF, erythropoietin and other cytokines, receptors, cystic fibrosis transmembrane conductance regulator (CFTR), tumor suppressors, antisense RNAs, and vaccine antigens. The vector comprises a sequence capable of providing retroviral long terminal repeats (LTRs), a sequence required for reverse transcription, a retroviral packaging sequence, and the gene sequence of interest. A DNA construct includes the LTRs necessary for host cell genome incorporation and expression. Following synthesis the viral DNA is integrated into cellular DNA so that the ends of the LTRs are directly joined to cellular sequences to form a stable structure (e.g., the provirus). The vector component necessary for reverse transcription does not necessarily include sequence coding for reverse transcriptase, but rather, includes a replication initiation site and a polypurine tract. A packaging signal, preferably specific for the retroviral vector of interest, is included in the vector. Donor and acceptor splice sites and internal ribosome entry sites (IRES) may also be present in the replication defective virus vectors. The splice sites enable the expression of additional heterologous inserted nucleic acid sequences.

To minimize the chance of producing infectious viral particles once the retroviral vector DNA is integrated into host cellular DNA, the replication defective virus vector need not include one or more of the sequences corresponding to the viral genes gag, coding for the viral core proteins, pol, coding for the viral RNA-dependent DNA polymerase (reverse transcriptase and other enzymatic proteins), or env, coding for the viral envelope proteins. The sequences can be omitted or rendered defective by mutagenesis.

For gene transcription from the replication defective virus vectors packaged by a MDEV cell line of the present invention, the gene of interest may be linked to a heterologous promoter. The selection of a suitable promoter is well within the level of ordinary skill in the art. A wide variety of promoters have been described in the literature including both viral and cellular promoters. Viral promoters include the immediate early cytomegalovirus promoter (Boshart et al., *Cell* 41:521–530, 1985), the murine leukemia virus (MLV) LTR promoter (Weiss et al., *RNA Tumor Viruses,* Cold Spring Harbor Laboratory Press, Cold Spring Harbor, N.Y., p766 (1985)) the SV40 promoter (Subramani et al., *Mol. Cell. Biol.* 1:854–864, 1981) and the like. Cellular promoters include but are not limited to the mouse metallothionien-1 promoter (Palmiter et al., U.S. Pat. No. 4,579,821). Alternative splicing may also be exploited to facilitate the expression of polycistronic genes in the vector. In this strategy, one of the proteins encoded by the vector is translated from the full length vector RNA while partial splicing from a splice donor site near the 5' LTR to a splice acceptor just upstream of a downstream gene yields a transcript that encodes the downstream gene product. Because vector replication involves an RNA intermediate, construction of the vector containing inserted gene(s) should permit full-length transcription of vector genome.

The replication defective retrovirus vector particles packaged by the MDEV cell lines in accordance with the present invention will often contain at least one exogenous (heterologous) gene. Heterologous genes encompass DNA (or RNA corresponding to the DNA) encoding proteins or peptides of interest and RNA molecules such as antisense RNA. DNA sequences encoding proteins of interest include genes, cDNAs and minigenes. For use in gene therapy, a retroviral vector will contain the heterologous gene or other DNA which is desired to be transferred to the cells of the intended recipient. Heterologous genes can code for the replacement or substitute of a defective or missing enzyme or other protein, RNA molecule or ribozyme in the patient, or encode therapeutic proteins or RNA molecules normally not present in the patient. The enzyme or other protein may function within a cell, or may be secreted and circulate in the body, such as hormones and blood factors. Genes which code for proteins whose levels do not have to be precisely controlled, and/or genes which cause disease by virtue of a single defect, are particularly suitable for insertion in a retroviral vector packaged by a MDEV packaging cell line of the present invention.

Selectable markers can also be included in the replication defective retroviral vectors packaged according to the present invention, for investigative or experimental purposes, or to provide a means to select for cells containing the replication defective retroviral vectors. These markers include the neomycin and hygromycin phosphotransferase genes that confer resistance to G418 and hygromycin, respectively. Other markers include the mutant mouse dihydrofolate reductase gene (dhfr*) which confers resistance to methotrexate, the bacterial gpt gene which allows cells to grow in medium containing mycophenolic acid, xanthine, and aminopterin, the bacterial hisD gene which allows cells to grow in medium without histidine but containing histidinol, and the multidrug resistant gene (mdr) which confers resistance to a variety of drugs. These markers are dominant selectable markers and allow chemical selection of most cells expressing these genes.

Suicide genes may also be contained within the vectors packaged by the MDEV cell lines of the present invention. Such genes provide a means to selectively kill cells containing the retroviral RNA. For example, the tk gene (Culver et al., *Science* 256:1550–1552 (1992)) may be used in combination with gancyclovir to selectively kill transduced cells.

The exogenous gene for insertion in the vector can be an intronless cDNA copy of an mRNA encoding a gene product of interest. Large inserts can be placed in the replication defective retroviral vectors, but generally the gene(s) of interest and any attendant regulatory sequences should be no more than up to approximately 8 to 11 kb in size. The 5' and 3' noncoding regions of the cDNA can be trimmed to reduce the size of the insert and to remove potential polyadenylation signals that may occur in the 3' end of cDNAs. It may be preferable to insert the cDNA in the same transcriptional orientation as the viral LTR. Antisense RNAs can be expressed by reversing the orientation of the cDNA with respect to a promoter. Other inserts include intronless "minigenes" which include normal genes from which the introns have been removed and those with trucated coding regions. Entire genes containing introns can also be inserted, and typically will be inserted in reverse orientation to prevent removal of the introns during vector replication.

Packaging cell lines of the present invention may be constructed and optimized using a variety of strategies. In general, such strategies are designed to reduce the chance of recombination between a helper construct (i.e., one or more constructs that provide trans-acting proteins required for production of replication defective retroviral vector particles) and the vector that may result in the production of helper virus. In this context "helper virus" means undesirable replication-competent retrovirus produced from the integrated proviral genome in some packaging cells by genetic recombination and repair of the defective retroviral vector proviral genome. Strategies include but are not limited to helper constructs in which the packaging signal(s) have been deleted, helper constructs in which the gag, pol and env genes are split into two or more separate transcriptional units, e.g., containing gag-pol and env, or helper constructs in which the gag-pol and env genes are split into two separate transcriptional units and which contain mutations (e.g., by insertions of linkers) and deletions in the gag-pol and env transcriptional units. In addition, the 3' LTRs in separate transcriptional units can be replaced with polyadenylation signals from SV40, thereby requiring an additional recombinational event to generate helper virus. Avoidance of homologous overlap between vector and helper virus sequences in the MDEV packaging cells decreases the chance of helper virus production. This can be accomplished by removing as much of the helper virus sequences from the vector as possible. Suitable helper constructs are cotransfected with the vector of the present invention thus providing the required trans-acting proteins and allowing virus particle production. Trans-acting proteins may also be provided by packaging cell lines that are designed to provide all viral proteins but not to package or transmit the RNAs encoding these functions. These packaging cell lines contain the replication defective retroviral vector genome of interest, and expression of the trans-acting proteins permits the production of packaged retroviral vectors. For the construction of packaging cell lines suitable for use in the present invention, the trans-acting viral proteins may be provided in a transient or inducible manner. Trans-acting viral genes may be placed under the control of an inducible promoter such as the tetracycline-responsive promoter (Gossen and Bujard, *Proc. Natl. Acad. Sci. U.S.A.* 89:5547–5551, 1992 and Pescini et al., *Biochem. Biophys. Res. Comm.* 202:1664–1667, 1994). For packaging cell lines containing trans-acting genes under the control of regulated promoters, packaging may be indicated by inducing the promoter.

Cells suitable for use in preparing packaging cell lines of the present invention are derived from vertebrates and include, for example, avian, primate, porcine, human, murine, canine etc. Particularly preferred cells for preparing packaging cells are NIH 3T3, however, other suitable cells are readily available.

The MDEV packaging cells are produced by introducing DNA constructs which direct the expression of trans-acting Gag, Pol and MDEV envelope proteins that are required for packaging replication defective retroviral particles. Methods for introducing such constructs include, for example, calcium phosphate precipitation (Wigler et al., *Cell* 14:725 (1978); Corsaro and Pearson, *Somatic Cell Genetics* 7:603 (1981); Graham and Van der Eb, *Virology* 52:456 (1973); lipofection (Felgner et al., *Proc. Natl. Acad. Sci. U.S.A.* 84:7413–7417 (1987)), microinjection and electroporation (Neumann et al., *EMBO J.* 1:841–845 (1982)). The cells can also be transduced with virus, such as SV40, CMV and the like. In the case of viral vectors, cloned DNA molecules may be introduced by infection of susceptible cells with viral particles. The gag and pol genes may be derived from a wide variety of retroviruses, and within a preferred embodiment the gag and pol genes are derived from Moloney murine leukemia virus (MoMLV).

In an alternative embodiment of the present invention, methods are provided for transiently producing replication-defective virus particles by transducing or transfecting a vertebrate cell with a first vector comprising a retrovirus gag gene, a second vector comprising a retrovirus pol gene, a third vector comprising a MDEV env gene, or a fragment thereof encoding a receptor binding fragment; and a replication defective virus particle which comprises virus RNA transcribed from a recombinant DNA provirus, the provirus comprising virus long terminal repeat sequences (LTRs), a retrovirus packaging sequence, and a heterologous gene, or a vector comprising said provirus, wherein the cell is capable of expressing and assembling retroviral proteins. The transfected or transformed cell transiently expresses the proteins encoded by the *M. dunni* endogenous virus env gene, or a fragment of the Env protein capable of binding to the *M. dunni* endogenous receptor on a target cell, and also expresses the retrovirus Gag and Pol proteins as well as the product encoded by the heterologous gene. When expressed, a replication-defective retroviral vector particle is produced which can bind to *M. dunni* endogenous virus receptors of target cells. Transient packaging can also be accomplished using a first vector which contains both the retrovirus gag and pol genes in place of the first and second vectors described above. (See, for example, Burns et al., *Proc. Natl. Acad. Sci. U.S.A.* 90:8033–8037 (1993); Naviux et al., *J. Virol.* 70:5701–5705 (1996); and Soneska et al., *Nuc. Acid. Res.* 23:628–633 (1995)). Other methods for transiently producing replication defective virus particles are well known to the skilled artisan. The replication defective virus particles produced transiently or by the packaging cell lines of the present invention all are capable of binding to MDEV receptors on target cells and provide means for the transfer of a wide variety of heterologous nucleic acid segments.

Using the MDEV packaging cell lines of the present invention, replication defective retroviral vectors are assembled into corresponding retroviral particles by surrounding the recombinant viral RNA with the Gag and Pol proteins to form a core particle and encapsulating the core particle in a membrane containing the env encoded protein. Thus, a packaging cell of the present invention provides replication defective retroviral particles capable of transducing cells (i.e., an infectious virus having a ribonucleoprotein core particle surrounded by a membrane containing MDEV envelope protein, or fragments thereof which are capable of binding to the MDEV receptor on target cells) containing the vectors as described herein.

The production of undesirable helper virus can be detected in a variety of ways, including, e.g., vector rescue assays in which cells containing but not producing a selectable replication-defective viral vector are transduced with the test virus and assayed for production of the vector. Rescue of the vector can be detected by passaging the cells to allow virus spread and assaying medium exposed to these cells for the selectable viral vector in a standard colony assay. Representative assays include the $S^+L^-$ assay described by Bassin et al. (*Nature* 229:5646, (1971), incorporated herein by reference) and marker rescue described by Miller et al. (*Meth. Enzymol.* 217:581–599 (1993), incorporated herein by reference).

The replication defective retroviral vectors packaged by the MDEV packaging cell lines of the present invention provide the means for gene transfer in a wide range of animals species, including, e.g., experimental and domestic animals, livestock (e.g., sheep, cows, horses), birds (e.g., chickens), cats, rats, mice, hamsters, dogs, monkeys and primates (e.g., chimpanzees, macaques, and monkeys, and humans). For livestock uses, for example, the particles produced according to the invention are useful for infecting cells in preimplantation embryos, which embryos when implanted in an animal creates a transgenic animal or an animal which expresses a gene product that it would normally not produce.

The replication defective retroviral particles packaged in a MDEV packaging cell line of the invention are used to infect (transduce) target cells, such as, for example, those which are defective in expression of the gene of interest, or which can act to secrete the desired protein. By transduction is meant the process by which non-viral genes are transferred and expressed in a host cell by a viral vector. Transduction can take place ex vivo or in vivo. When the transduction is performed ex vivo, typically the targeted cells, e.g., lymphocytes, bone marrow, hematopoietic cells and hematopoietic stem cells, fibroblasts, hepatocytes, endothelial cells, benign or malignant tumor cells, etc., are autologous in that they have been removed from the individual in need of the gene product of interest, but allogeneic or even xenogeneic cells may also be employed. The cells are infected by the replication defective virus particles containing the gene of interest, and the cells are returned (or transplanted) to the host. When the transduction of the host cells is ex vivo, typically medium containing the recombinant replication defective virus particles is incubated with the target cells. The target cells may be cultivated ex vivo to expand their numbers in primary cell cultures. Transduction is typically during the early days of host cell culture, and may be accomplished by co-cultivating the target cells with a cell line producing replication defective virus vectors. The target cells are not necessarily cultured prior to transduction and replacement in the host patient.

For in vivo transduction, the replication defective virus particles can be administered to the host in a wide variety of ways. The particular mode of administration will depend upon several factors, including, among others, the particular use intended, the host being treated, the tissue targeted for transduction, the gene product of interest, the general health of the patient, etc., but will generally be administered intradermally, subcutaneously, intramuscularly, topically (e.g., aerosol, such as via a nebulizer), intravenously, intraperitoneally, or the like. Thus, the vectors may be administered to tissues and organs (e.g., via a catheter) such as the lungs, bladder, urethra, uterus, liver, heart and circulatory system, kidney, bone marrow, brain, lymphoid tissues, stomach, small intestine, large intestine, colon and prostate.

The dosages of the replication defective virus vectors produced according to the invention will be determined through empirical experiments such as dose escalation studies and the like. It must be kept in mind that the materials of the present invention may be employed in serious disease states, that is, life-threatening or potentially life threatening situations. In such cases, in view of the ability of the replication defective virus particles produced by the present invention to infect a wide variety of vertebrate cells, it is possible and may be felt desirable by the treating physician to administer substantial excesses of these viral particles.

The following examples are offered by way of illustration, not by way of limitation.

Prior to setting forth the specific examples, nomenclature, cells and cell lines used throughout the examples are provided.

EXAMPLE I

Molecular Cloning of *Mus dunni* Endogenous Virus

Nomenclature. As used in this and all Examples, cells that contain a retroviral vector and/or contain and express a retrovirus are indicated by the cell name followed by a slash and the name of the vector, e.g., dunni/LN are *Mus dunni* cells that contain the LN retroviral vector and G355/LAPSN are G355 cat cells containing the retroviral vector LAPSN. A retroviral vector in its viral form is indicated by the vector name followed, in parentheses, by the name of the helper virus or packaging cells used to pseudotype the vector, e.g., LAPSN(PT67) refers to the viral form of the LAPSN retroviral vector packaged by PT67 cells, which express the 10A1 murine leukemia virus envelope and LAPSN(PA317) refers to the viral form of the LAPSN retroviral vector packaged by PA317 cells, which express the amphotropic MLV envelope. In this example, the pseudotype of a retroviral vector refers only to the viral envelope protein present on the vector virions that determines the cell-surface receptor utilization pattern of the vector, irrespective of the origin of the Gag and Pol proteins.

*Cell Culture.* D17 dog cells (ATCC CCL 183), LGPS cells (Miller et al., *J. Virol.* 65:2220–2224 (1991)), and the packaging cell lines PA317 (Miller and Buttimore, *Mol. Cell. Biol.* 6:2895–2902 (1986) and U.S. Pat. No. 4,861,719), PG13 (Miller et al., *J. Virol.* (1991) and U.S. Pat. No. 5,470,726), PT67 (Miller and Chen, *J. Virol.* 70:5564–5571 (1996)), PM571 ((Miller and Miller, *J. Virol.* 65:78–84 (1992)), FLYRD (Cosset et al., *J. Virol.* 69:7430–7436 (1995)) and PE501 (Miller et al., *BioTechniques* 7:980–990 (1989) were grown in Dulbecco's modified Eagle's medium with 10% fetal bovine serum (FBS). G355 feline embryonic glial cells (Dunn et al., *J. Virol.* 67:4704–4711 (1993)) were grown in McCoy's modified Eagle's medium supplemented with 15% FBS. CHO cells were grown in AMEM with 5% FBS.

This Example describes the molecular cloning of *M. dunni* endogenous virus (MDEV) and relationship by nucleic acid hybridization to other retroviruses.

To isolate a clone of MDEV, a strategy was initially employed that involved use of radiolabeled DNA from a variety of cloned retroviruses as potential probes for the detection of plasmids containing MDEV sequences. However, probes made using ecotropic Moloney murine leukemia virus (MoMLV), xenotropic NZB virus, gibbon ape leukemia virus (GALV), polytropic 98D virus, mouse mammary tumor virus (MMTV), amphotropic virus (AM-MLV), RD114, and two species of human endogenous retroviral elements (HERV-K and HERV-H) failed to hybridize to MDEV on Northern blots of RNA extracted from MDEV-producing *M. dunni* cells, even under low stringency conditions, and were therefore not useful as probes with which to clone the virus.

A second strategy, which was successful in cloning MDEV, involved construction of a plasmid library from unintegrated viral DNA and screening of the library for clones containing MDEV sequences by using a probe derived from viral RNA. The source of MDEV virus used for the preparation of viral RNA, cDNA for the Southern probe and for host range studies was a clone of G355/LAPSN+MDEV cells selected for the production of high titer LAPSN ($10^6$ focus forming units (FFU)/ml on *M. dunni* cells), called GL8c16 cells.

Extrachromosomal DNA was harvested from *M. dunni* cells 24 hours after infection with a mixture of MDEV and LAPSN virus. On day one, *M. dunni* cells were seeded at $2 \times 10^6$ cells per 14 cm-diameter dish in 60 dishes. On day two, the cells were infected with MDEV plus LAPSN virus produced from GL8c16 cells (at a multiplicity of infection (MOI) of 2.5 based on the LAPSN vector) with 4 μg/ml Polybrene. Twenty-four hours after infection, extrachromosomal DNA was isolated by the method of Hirt (Hirt, B., *J. Mol. Biol.* 26:365–369 (1967); incorporated herein by reference in its entirety). Supercoiled DNA, predicted to contain circular LAPSN and MDEV reverse transcription products with one and two LTRs, was further purified from contaminating chromosomal DNA by three serial centrifugations in CsCl containing ethidium bromide (Radloff et al., *Proc. Natl. Acad. Sci. U.S.A.* 57:1514–1521 (1967); which incorporated herein by reference in its entirety). DNA was purified from the CsCl by multiple sodium acetate/ethanol precipitations, and washed with 70% ethanol. The presence of the LAPSN vector provided a positive control for the cloning procedure.

Aliquots of the purified viral DNA were digested with a panel of restriction enzymes, electrophoresed on 0.8% agarose gel, and transferred to a nylon membrane (Hybond). The nylon membrane was hybridized with radiolabeled cDNA made from RNA extracted from virus produced from G355 cat cells infected with MDEV and LAPSN (GL8c16). The viral RNA was isolated from virus produced from cat cells, rather than from *M. dunni* cells, to minimize the presence of sequences reactive with *M. dunni* DNA sequences that were expected to be present in the viral DNA library. On day one, GL8c16 cells were seeded at $1 \times 10^6$ cells/10 cm plate. On day three cells were fed with fresh medium, and virus-containing medium was harvested 24 hours later. This process was repeated on days 4 and 5. Harvested medium was filtered using 0.45 μm bottle top filters (Nalgene) and, if not used immediately, was stored at $-70°$ C. Filtered virus-containing medium (approximately 200 ml) was layered on top of 20% sucrose (in phosphate-buffered saline; 4 ml per tube) in 6×30 ml Beckman SW28 ultracentrifuge tubes. Virus particles were pelleted at 26,000 rpm in a Beckman SW28 swinging bucket rotor for 2 h at $4°$ C. After removing the supernatant, pellets were resuspended in a total of approximately 500 μl ice cold TNE buffer (10 mM Tris, pH 7.5, 100 mM NaCl, 1 mM EDTA).

Viral RNA was extracted from the pellets as described (MacKenzie et al., *J. Virol.* 68:6924–6932 (1994); incorporated herein by reference in its entirety) and precipitated at $70°$ C., overnight. RNA was pelleted in a microcentrifuge (EPPENDORF) at $4°$ C. for 30 minutes, and the pellet was resuspended in 1 ml distilled water. Polyadenylated RNA was selected using a cellulose affinity column (Mini-Oligo (dT) Cellulose Spin Column Kit (5'→3', Boulder, Colo.)) according to the manufacturer's instructions.

Complementary DNA (cDNA) was reverse transcribed in vitro from the viral RNA using the polyadenylated RNA isolated from 400 ml of virus-containing medium per 50 μl reaction. Reaction conditions were similar to those described (Arya et al., *Prep. Biochem.* 10:483–493 (1980); incorporated herein by reference in its entirety). The reaction mix contained viral RNA in 10 μl distilled water, 50 mM Tris, pH 8.1, 10 mM DTT, 50 mM NaCl, 3 mM magnesium acetate, 0.6 mM magnesium chloride, 1 mM each of dGTP, DATP, and dTTP, 100 μCi α-$^{32}$P-dCTP (800 Ci/mmol), 500 μg/ml oligo dT primers, 0.5 units/μl Promega RNasin, and 70 units of MoMLV reverse transcriptase (Stratagene). The reaction was incubated at $37°$ C. for one hour and cDNAs were separated from free nucleotides using a size exclusion column (Sephadex G-50). This probe was then tested by Northern blot analysis for specific hybridization to MDEV transcripts and not to RNA from uninfected cells or to RNA from cells infected with amphotropic virus.

The Southern blot was analyzed to determine which enzymes would be useful in cloning the *Mus dunni* endogenous virus (MDEV) DNA. Eco RI appeared to cut only once within MDEV. Based on the results, the supercoiled DNA was digested with Eco RI and cloned into the BLUESCRIPT plasmid (Stratagene), generating a library with a complexity of $10^5$. The library was screened using standard procedures, and positive clones were confirmed by Southern blot analysis (Maniatis et al., *Molecular Cloning: a Laboratory Manual*, CSH Laboratory Press: Cold Spring Harbor, N.Y. (1989)). The MDEV plus LAPSN cDNA probe identified multiple clones of LAPSN and clones of a retrovirus presumed to be MDEV, containing both one and two LTRs, from the library. No positive clones other than LAPSN and the presumptive MDEV were identified. One positive clone, pMDEV9, was selected for further sequence analysis.

To determine the nucleotide sequence of pMDEV9, portions of the MDEV clone pMDEV9 were subcloned into pBSII KS+ and deletions were made with exonuclease III using the method of Clark and Henikoff (in *Methods in Molecular Biology, Vol.* 31: *Protocols for Gene Analysis,* ed. Harwood, A., Humane Press, Totowa, N.J. (1994); incorporated herein by reference in its entirety). Sequencing was performed on the nested deletion constructs using dye primer ABI PRISM sequencing kits and analyzed with a 373A DNA sequencer and sequence analysis software (Applied Biosystems, Foster City, Calif.). Regions of poor sequence were resequenced after making appropriate primers and using the ABI PRISM dye terminator kits. Both strands of MDEV were completely sequenced, and the sequences were assembled into contigs and further analyzed using SEQUENCHER 3.0 (Gene Codes Corporation, Inc., Ann Arbor, Mich.).

The nucleotides of the MDEV genome were numbered beginning with the presumptive cap site, the first nucleotide of the R region. This putative cap site was identified by comparison of MDEV to the VL30 element VL3 (accession X03489) in which the cap site has been mapped (Rotman et al., *Nuc. Acids Res.* 14:645–656 (1986)). The complete nucleotide sequence of MDEV (SEQ ID NO: 1) and the deduced amino acid sequences of the glycosylated Gag (SEQ ID NO: 2), Gag (SEQ ID NO: 3), Pol (SEQ ID NO: 4) and Env (SEQ ID NO: 5) of MDEV have been deposited into GenBank under accession number AF053745.

To determine whether the retroviral sequence in one of the presumptive MDEV clones (pMDEV9) was related to the virus which was activated from the *M. dunni* cells, cytoplasmic RNA samples isolated from both activated and unactivated *M. dunni*-v (a type of *Mus dunni* tail fibroblast that when grown to confluency, secretes molecules that render the culture medium viscous (Eiden et al., *J. Virol.* 67:4056–4061 (1993) and Eiden et al., *J. Virol.* 68:626–631 (1994)) and from uninfected and MDEV-infected G355 cells were analyzed by Northern blot, using the insert from pMDEV9 as a probe. The probe hybridized to 8.6 kb genomic and 3.7 kb subgenomic RNAs in both activated *M. dunni*-v cells and G355 cells producing MDEV, demonstrating the specificity of the probe for the MDEV transcripts present in infected cells. The pMDEV9 probe did not hybridize to RNA from cells infected with AM-MLV plus LAPSN vector, indicating limited sequence similarity between MDEV and AM-MLV or LAPSN. The probe did not hybridize to RNA from unactivated *M. dunni* cells transduced with LAPSN vector which do not produce MDEV or to uninfected G355 cells, indicating that MDEV is not normally transcribed in unactivated *M. dunni* cells or uninfected G355 cells. MDEV was not successfully activated from *M. dunni*-nv (a type of *M. dunni* tail fibroblast that when grown to confluency does not secrete molecules that render the culture medium viscous). Once activated, MDEV can infect and replicate in *M. dunni*-v and many other cells without further chemical treatment, indicating that all of the genes required for virion production and virus replication are present, and that the viral promoter can remain active.

MDEV is endogenous to the *M. dunni* genome, and related sequences are present in the genomes of laboratory strains of mice. To determine whether MDEV was actually present in the germline of the *M. dunni* mouse and not an acquired contaminant of the *M. dunni* cell line, Southern analysis was performed using the viral DNA insert from pMDEV9 as a probe to examine genomic DNA from a *M. dunni* cell line and from the spleens of two *M. dunni* mice. The genomic DNA samples were digested with Eco RI, which cuts once within the MDEV provirus, to allow detection of MDEV, its copy number, and whether its integration site(s) were the same in the various samples. Two strongly hybridizing bands were visible in DNA from the *M. dunni* cells and these same bands were present in DNA from both *M. dunni* mice, indicating that MDEV is present in the germline of the *M. dunni* mouse at the same integration site as in the cell line. Given that the entire MDEV provirus was used as a probe, these two bands probably represent the two halves of one copy of MDEV. In addition, a less intense band was visible at approximately 23 kb in the DNA of both mice, and at still lower intensity in the DNA from the *M. dunni* cell line. This third band suggests the presence of a second element closely related to MDEV.

Given the possibility that the DNA band at 23 kb may not have transferred efficiently to the filter, or that the band was the result of a partially-digested DNA fragment, the number of copies of elements closely related to MDEV was determined by Southern blot analysis of Xho I-digested DNA. Digestion of DNA containing a provirus with Xho I sites would be expected to produce a fragment of approximately 9 kb because there is one Xho I site in each LTR of the MDEV clone. Therefore, using the entire MDEV provirus as a probe on this blot, a 9 kb band was observed that coincides with that expected from MDEV in the *M. dunni* cells. Xho I-digested *M. dunni* DNA also produced DNA fragments of approximately 6 and 3 kb which hybridized less well to MDEV. Using MDEV pol and env DNA fragments as probes on this blot, the band at 6 kb hybridized to MDEV pol-related sequences and the band at 3 kb hybridized to MDEV env-related sequences, while the presumptive MDEV band at 9 kb hybridized to both probes. These data suggest that the 3 and 6 kb bands may comprise a second, MDEV-related element with a Xho I site in each LTR and an additional, internal Xho I site. This element may also be responsible for the large, somewhat indistinct ~23 kb band seen on the blot of Eco RI-digested DNA.

In addition to the elements described above that hybridized with the MDEV probe, the high level of background hybridization in the samples containing *M. dunni* DNA indicated that there are sequences weakly related to MDEV that are dispersed throughout the genome. In contrast, cell lines derived from laboratory strains of mice contain very little MDEV-related DNA. Bands of identical sizes (approximately 9 kb) and with the same relative intensities were visible in EcoRI-digested DNA from NIH 3T3, Balb/c 3T3, and C2C12 cells (derived from NIH Swiss, Balb/c and C3H mice, respectively). This result indicated that one copy of a retroviral element related to MDEV is present at the same site in these genomes, consistent with integration of the element into the genome prior to the divergence of these strains.

The relatively faint hybridization of MDEV to these samples compared with *M. dunni* DNA indicated that the sequences are related, but not identical to MDEV. In addition, no hybridization of the pMDEV9 probe was detected to DNA or RNA from D17 dog cells infected by Balb/c 3T3 IdU induced virus (BIRV), while a probe made from 98D polytropic virus did recognize BIRV sequences in these samples, indicating that the MDEV-related sequences present in the Balb/c 3T3 cells were not BIRV DNA. While the majority of endogenous murine viruses are found in many copies per genome, by Southern blot analysis, one copy was found of a provirus apparently identical to the MDEV clone in *M. dunni* DNA, another closely-related provirus, and a background of other sequences with some similarity to MDEV.

The entire MDEV provirus was used as a probe on a Southern blot of genomic DNA from a variety of animals in addition to mice. While MDEV was clearly present in *M. dunni* DNA, no hybridization to the genomic DNA of cells derived from hamsters, rats, quails, cats, dogs, baboons, or humans was detectable even under low stringency conditions (40° C., 2× SSC, 0.1% SDS wash). Sequences related to MDEV were only seen in the C2C12 mouse cells. These results further suggest the unusual content of the MDEV genome, as well as the rarity of this virus or viruses closely related to it.

EXAMPLE II

Construction and Function of MDEV Envelope Expression Vectors

To make retrovirus packaging cells for production of vectors with a *Mus dunni* endogenous virus (MDEV) pseudotype, MDEV env expression plasmids were constructed. Various MDEV env expression plasmids were tested by introducing the plasmids into LGPS cells that contained a retroviral vector capable of directing the expression of the MoMLV gag and pol genes and measuring the titer of vector produced.

Six molecular clones of MDEV were isolated from a library of extrachromosomal DNA from G355 cat cells infected one day earlier with MDEV essentially as described in Example I and by Bonham et al. (*J. Virol.* 71:4663–4670 (1997), which is incorporated by reference herein in its entirety). As described in detail in Example I, a library of unintegrated viral DNA was produced by digesting the extrachromosomal circular DNA from MDEV-infected G355 cells with Eco RI, and cloning it into pBSII KS+ (Stratagene Cloning Systems, La Jolla, Calif.). The library was screened using standard procedures and positive clones were confirmed by Southern blot analysis (Maniatis et al., *Molecular Cloning: a Laboratory Manual*, CSH Laboratory Press: Cold Spring Harbor, N.Y. (1989)). Sequence analysis of the clones demonstrated that the MDEV Eco RI site was in the pol gene. Different orientations of the virus, the presence of one versus two LTRs, and the presence of extraneous DNA fragments in the PBSII KS+ Eco RI cloning site demonstrated that the clones were independent.

A vector-rescue assay was employed to determine whether the molecular clones were competent to provide gag, pol, and env gene products in trans to a vector. Each of the six clones was digested with Eco RI, religated at low concentration to rejoin the pol gene, and transfected into G355/LAPSN cells, but none of the clones were competent to rescue the LAPSN vector (Miller et al., *Proc. Natl. Acad. Sci. U.S.A.* 91:78–82, (1994)). However, three clones were competent to rescue LAPSN when cotransfected with pSX2 (Miller and Chen, *J. Virol.* 70:5564–5571 (1996)), a plasmid that expresses the 10A1 MLV envelope protein. This indicated that these clones can express functional Gag and Pol proteins after religation of the pol gene, but not a functional Env protein. Sequence analysis of pMDEV9, described below, demonstrated that there was a +1 frame-shift in the envelope gene. Sequence analysis of the corresponding region of the other five clones revealed the same frame-shift, indicating that they had originated from a common defective virus.

Sequence analysis of the env region of the pMDEV9 clone compared to other retroviral genome structures indicated that there was a frame-shift mutation that resulted in a truncated protein. To determine the nature of the envelope frame-shift mutations, the polymerase chain reaction (PCR) was performed with Taq polymerase (Promega) according to the manufacturers instructions with the primers 5' TTG GTG GCC TGA TCT CAC ACC TG 3' (SEQ ID NO: 5) and 5' CTC TCC TAT TTT GCA GTA CTA CCT C 3' (SEQ ID NO: 7). Thermocycling was carried out with one cycle (95° C. for 10 min); 30 cycles (94° C. for 1 min., 71° C. for 1 min., 72° C. for 2 min.); and one cycle (72° C. for 5 min.). Templates included genomic DNA from unactivated *M. dunni* cells and G355/LAPSN+MDEV cells, as well as negative controls including no template and DNA from uninfected G355 cells. Amplification reactions performed on DNA from uninfected G355 cells or performed with no DNA did not yield detectable product. The PCR products from both unactivated *Mus dunni* cell DNA and G355/LAPSN+MDEV DNA were then cloned into plasmid pT7Blue (Novagen) according to the manufacturer's protocol. Several clones from separate PCR amplifications of various templates were sequenced. Sequencing demonstrated that the frame-shift was due to an extra A residue at position 6168 within the first variable region of env generating the +1 frame-shift. In addition, the sequence revealed additional changes peripheral to the frame-shift that affect the protein sequence. As it was unknown whether these additional changes represented errors by Taq polymerase, the mutation was corrected in two ways by site-directed mutagenesis.

In a first method to correct the mutation, the env mutation was corrected by site-directed mutagenesis to delete the single extra base pair that resulted in the frame-shift. To initiate the correction, the env region was subcloned as a 2.8 kb Bam HI-Xho I fragment of pMDEV9 into Bam HI-Sal I linearized pBSII KS+. The resulting plasmid, pEA9, was used as a template for the site-directed mutagenesis to correct the frame-shift mutation using the QUICKCHANGE site-directed mutagenesis kit (Stratagene Cloning Systems). Two primers MDEVMUTF: 5'CAG GGT CAG AAA GGA AAG CTG CAA CAA GAA TG 3'; (SEQ ID NO: 8) and MDEVMUTR: 5' CAT TCT TGT TGC AGC TTT CCT TTC TGA CCC TG 3'; (SEQ ID NO: 9) were designed to create a plasmid containing the corrected env gene. The primers and the pEA9 template were subjected to thermocycling (one cycle at 95° C. for 30 seconds, 16 cycles (95° C. for 30 seconds, 55° C. for 1 minute, 68° C. for 24 minutes)). The products were digested with Dpn I and transformed into *E. coli*.

Plasmid DNA prepared from selected transformants were subjected to sequence analysis to identify a plasmid containing the corrected env gene. One clone containing the frame-shift correction, which was confirmed by sequence analysis, designated pEA9corr, was digested with Bam HI, Xmn I and Ahd I to isolate the 2.17 kb Bam HI-Xmn I env gene fragment. The 2.17 kb Bam HI-Xmn I fragment was then subcloned into the 3948 bp fragment of pSX2 (Miller and Chen, *J. Virol.* 70:5564–5571, 1996) that had been prepared by digestion with Bsa Bi and partial digestion with Bam HI to generate pMDEV9ex. The plasmid, pMDEV9ex, contained the corrected env gene in the correct orientation relative to the pSX2 backbone.

In a second method to build a MDEV env expression plasmid with an intact MDEV env gene, wild-type env gene sequences were obtained by PCR amplification of templates containing the wild-type MDEV sequences using primers that overlap the start and stop codons of the MDEV env. The templates for amplification included the plasmid pEA9corr, which contains the same envelope sequence as pMDEV9ex, DNA from unactivated *M. dunni* cells, and DNA from G355/LAPSN+MDEV cells. DNA from uninfected G355 cells and no DNA were used as negative controls for the PCR amplification reactions. The primers (MDEV Env 1 5' GCC CAC CGT GTG CCA CCA TGA AGA AAC CCA CGA AGA CAA C 3'; (SEQ ID NO: 10) and MDEV Env 2: 5' GCG GTT AAC ATA GCT CTA ATC CTA GAG CGA G 3'; (SEQ ID NO: 11)) were designed to amplify a fragment encoding the wild-type MDEV env gene flanked on the 5' end by a near consensus sequence (Kozak, *Proc. Natl. Acad. Sci. U.S.A.* 92:2662–2666 (1995)) to optimize translation; an upstream Dra III site, and flanked on the 3' end by a Hpa I site. The primers and the template containing the wild-type env gene were amplified using Pwo polymerase (Boehringer Mannheim) at one cycle of 2 minutes at 94° C., 10 cycles (15 seconds at 94° C., 30 seconds at 62° C., 80 seconds at 72° C.), 20 cycles (15 seconds at 94° C., 30 seconds at 62° C., 80 seconds cumulatively increased by 20 seconds cycle at 72° C.), 7 minutes at 72° C. The reactions were stored at 4° C. The PCR products from unactivated *M. dunni* DNA or G355/LAPSN+MDEV DNA were ligated into Bsa BI-Dra III digested, blunt-ended pSX2. This vector fragment contained the MoMLV LTR promoter truncated at the 5' end to a Sau3 AI site just upstream of the transcriptional enhancers in the LTR, the MoMLV splice donor, the 10A1 splice acceptor, the early polyadenylation signal from SV40 and plasmid sequences derived from the poison-minus plasmid pML-1 (Lusky et al., *Nature* 293:79–81 (1981)). Plasmids containing envelope PCR products with wild-type MDEV env sequences in the correct orientation relative to the LTR were termed the PMEX series of plasmids. Twenty clones were selected for analysis. Plasmids pMEX$^{dunni}$ and pMEX$^{plasmid}$, respectively, contain an envelope amplified from DNA of unactivated *M. dunni* cells and an envelope amplified from plasmid DNA containing the same envelope as pMDEV9ex. Sequence analysis of pMEX$^{dunni}$ shows that the mutation in pMDEV9 was corrected.

To test functional activity, the twenty "pMex" MDEV envelope expression constructs were either transfected into the LGPS clone 91-22 (U.S. Pat. No. 5,470,726, incorporated herein by reference) that had been previously infected with the retroviral marker vector LAPSN (Miller et al., *Proc. Natl. Acad. Sci. U.S.A.* 91:78–82 (1994)) (yielding LGPS/LAPSN) or co-transfected with pLGPS (which expresses the Moloney MLV Gag and Pol) into G355/LAPSN. The LAPSN vector contains the neomycin resistance gene and a human placental alkaline phosphatase gene flanked by retroviral LTR's. The LGPS/LAPSN and G355/LAPSN cells do not contain the env gene required to produce functional vectors. As a negative control for viral vector production, an irrelevant plasmid was transfected into the cells. One day post-transfection the culture medium was changed. The culture medium from each transfection was harvested at two days post-transfection. The medium was centrifuged at 4,000× g for five minutes and aliquoted and stored at −80° C. until titration. Titers of LAPSN vector stocks were determined by plating D17 target cells on day 1 at 5×10$^4$ cells per 35 mm (diameter) well of a 6 well plate. The medium was replaced with fresh medium containing 4 μg/ml of Polybrene (Sigma, St. Louis, Mo.) and a dilution of the medium from the transfected cells in a final volume of 2 ml on day 2. The cells were fixed with glutaraldehyde and stained for alkaline phosphatase (AP) expression as described (Field-Berry et al., *Proc. Natl. Acad. Sci. U.S.A.* 89:693–697 (1992); which is incorporated herein by reference) on day 4. Twenty pMEX clones were screened to identify those capable of expressing functional envelope protein. All five clones amplified from plasmid DNA were functional. Five out of six clones amplified from G355/LAPSN+MDEV DNA were functional, but only two out of nine clones amplified from *M. dunni* cell DNA were functional. Elements related to MDEV exist in the *M. dunni* genome and some of the nonfunctional pMEX plasmids may carry related but defective envelopes.

The transfection experiments indicated that the various functional MDEV env expression plasmids function similarly. Table 1 provides a comparison of representative MDEV env expression plasmids, 10A1 env expression plasmid (pSX2) and an empty vector. While transfection of pBSII KS+ did not result in detectable packaging of LAPSN, transfection with any of these env expression plasmids did result in packaging of LAPSN. No differences were observed among the MDEV env expression plasmids, including those containing an MDEV env amplified from infected G355 cells. The similar function of MDEV env expression plasmids containing envelopes amplified from various sources indicates that they do not contain significant mutations. In each case, however, the LAPSN titers resulting from transfection of the MDEV env expression plasmids were lower than those achieved by transfection of pSX2. This may reflect the biology of the viruses, for 10A1 MLV replicates to much higher titers than does MDEV.

TABLE 1

Comparison of Representative MDEV env Expression Plasmids

| Plasmid | LAPSN titer (AP$^+$ FFU/ml) |
| --- | --- |
| PBSII KS+ | <5 |
| pSX2 | 1 × 10$^5$ |
| pMDEV9ex | 2 × 10$^3$ |
| pMEX$^{plasmid}$ | 2 × 10$^3$ |
| pMEX$^{dunni}$ | 2 × 10$^3$ |

The titers are expressed as the mean of the values obtained from duplicate transfections.

Viral interference experiments were conducted that demonstrated that the LAPSN vector packaged by the MDEV Env in these transfection experiments used the same receptor as that used by wild-type MDEV.

EXAMPLE III

Generation and Evaluation of MDEV-Pseudotype Retrovirus Packaging Lines

Plasmid PMEX$^{dunni}$, which was constructed using *Mus dunni* DNA as a PCR template, gave among the best titers and was used in the construction of the MDEV packaging cells. To generate stable retrovirus packaging cells that expressed the MDEV Env protein, plasmids were introduced into cells of LGPS clone 91-22 that express MoMLV Gag-Pol proteins. On day 1, LGPS clone 91-22 cells were plated in three dishes at 5×10$^5$ per 6 cm diameter dish. On day 2, the cells were co-transfected with 5 μg DNA mixture of pMEX$^{dunni}$ and a hygromycin phosphotransferase (hpt) gene contained in the plasmid pSV2Δ130hyg (obtained from Paul Berg, Stanford University) by calcium phosphate precipitation (Miller et al., *BioTechniques* 7:980–990 (1989)). The ratio of selectable marker plasmid to env expression plasmid was 1:20. The medium was replaced on day 3, and on day 4 the cells were split into medium containing 0.4 mg/ml of hygromycin. Non-transfected control cells were completely killed by the hygromycin by day 10, so the cells were released from selection. Cells in the transfected cultures grew into clonal colonies, 38 of which were isolated by aspirating the medium from each dish, laying trypsin-soaked Whatman paper disks on the colonies, incubating the dish at 37° C. for 5 minutes, and placing the disks into individual wells of a 48-well plate. The colonies were then tested for ability to package the LAPSN vector. These 38 clones were designated PD, for packaging cells based on the *Mus dunni* endogenous virus envelope.

Packaging cell clones were subjected to two screening assays to determine which clone possessed the best ability to package a retroviral vector (Table 2). In a primary screen, aliquots of each clone were infected by LAPSN(PE501) at a multiplicity of infection (MOI) of approximately 1. Entry of the LAPSN vector pseudotyped by PE501 cells was unaffected by expression of the MDEV Env or MoMLV Gag-Pol proteins.

The primary screen was initialized by plating aliquots of the clones at $5 \times 10^4$ cells per 3.5 cm diameter well of a 6 well dish on day 1. On day 2, the medium was replaced with fresh medium containing 4 µg Polybrene per ml and 200 µl of LAPSN(PE501). The LAPSN(PE501) stocks had previously found to have a titer of $5 \times 10^5$ AP$^+$ FFU/ml on NIH 3T3 TK$^-$ cells using the procedure as described by Fields-Berry et al., *Proc. Natl. Acad. Sci. U.S.A.* 89:693–697 (1992); which is incorporated herein by reference). On day 3, the medium was replaced with medium containing no Polybrene. On day 4, the virus-containing medium was harvested and the titer determined by titrating the resulting LAPSN on D17 cells. The LAPSN vector titer was determined by plating D17 target cells at $1 \times 10^5$ or $2 \times 10^5$ cells per 3.5 cm diameter well of a 6-well dish on day 1. On day 2, the medium was replaced with medium containing 4 µg of Polybrene per ml, and the virus stock added. On day 4, the cells were stained for AP+ foci as previously described. Thirty-two of the thirty-eight clones were capable of packaging LAPSN. Nine clones that packaged LAPSN at high levels were subjected to a secondary screen to identify the clones that produce vectors at the highest titers.

The second screen was similar to the first, except that the clones were selected in G418 after infection by LAPSN (PE501) to be certain that all cells carried the LAPSN vector. The secondary screen was initialized by plating aliquots of the clones at $5 \times 10^4$ cells per 3.5 cm diameter well of a 6 well dish on day 1. Two wells were plated for each clone. On day 2, the medium was replaced with fresh medium containing 4 µg Polybrene per ml, and 400 µl of LAPSN(PE501) was added to one well for each clone. On day 4, the medium was replaced in both wells for each clone with medium containing 0.5 mg active G418 per ml. The cells were split 1:5 as they became confluent. Once all of the non-transduced cells had died in the presence of G418, the transduced clones were released from G418 selection.

To evaluate LAPSN production by the selected clones, each was plated at $2.5 \times 10^5$ per 3.5 cm diameter well on day 1. The medium was replaced on day 2 and harvested on day 3. LAPSN titers determined as in the primary screen, expressed as AP+ foci per ml of test medium, represent the mean of duplicate assays in which each value varied from the mean by no more than 17%. PD clone 223 (PD223) was also found to produce the highest titer of LAPSN in both the primary and secondary screens.

TABLE 2

Primary and Secondary Screens Identified the Best Packaging Clone

| Clone | 1° Screen LAPSN Titer | 2° Screen LAPSN Titer |
|-------|----------------------|----------------------|
| 208 | $4.9 \times 10^3$ | $6 \times 10^2$ |
| 209 | $7.5 \times 10^3$ | $4 \times 10^3$ |
| 217 | $1.4 \times 10^3$ | $4 \times 10^4$ |
| 223 | $1.3 \times 10^4$ | $1 \times 10^5$ |
| 229 | $1.2 \times 10^3$ | $2 \times 10^4$ |
| 230 | $1.4 \times 10^3$ | $2 \times 10^4$ |
| 235 | $1.4 \times 10^3$ | 100 |
| 260 | $6.5 \times 10^3$ | $3 \times 10^4$ |
| 276 | $8.2 \times 10^3$ | $1 \times 10^4$ |

Upon determining that PD223 packaged LAPSN at the highest titer, PD223/LAPSN cells were cloned to obtain a high titer producer line of LAPSN(PD223). After infection of PD223 with LAPSN(PA317), individual cells expressing AP on their surface were sorted into wells of a 96 well plate by FACS using an anti-AP antibody. Briefly, this assay comprised plating PD223 cells at $10^5$ cells per 3.5 cm diameter well of 6-well dishes on day 1. On day 2, the medium was replaced with fresh medium containing 4 µg/ml Polybrene, and either 200 µl (MOI~1) or 20 µl (MOI~0.1) of LAPSN(PA317)-containing medium was added. The LAPSN(PA317) had previously been found to have a titer of $1 \times 10^6$ AP$^+$ FFU/ml on NIH 3T3 cells.

The cells were prepared for FACS on day 4 by treatment with trypsin, dilution in 2 ml phosphate buffered saline (PBS) containing 2% FES and centrifugation at 1400 rpm for 5 minutes. The cell pellet was resuspended in 50 µl blocking solution from hybridoma 2.4G.2 containing 0.25 µl biotin-labeled monoclonal anti-human placental alkaline phosphatase clone 8B6 (Dako) antibody and incubated at room temperature in the dark for 30 minutes. The cells were resuspended in 2 ml PBS containing 2% FBS, centrifuged, and the cell pellets were resuspended in 50 µl PBS containing 2% FBS and 0.5 µl phycoerytherin-labeled streptavidin. The cells were incubated with the phycoerytherin-labeled strepavidin at room temperature in the dark for 30 minutes followed by resuspension in 2 ml PBS containing 2% FBS. The cells were pelleted by centrifugation followed by resuspension in 3 ml PBS containing 2% FBS, 1 µg/ml propidium iodide. The cells were sorted with a Becton Dickinson FACS Vantage Cell Sorter equipped with an automated cell disposition unit (San Jose, Calif.).

Dead cells and cellular debris were gated out based on forward and side scatter and propridium iodide staining. After gating, fluorescence profile showed two populations: the nontransduced population, which fluoresced at an intensity equal to nontransduced control cells, and a transduced population that fluoresced at a level ten times as intense as the control cells. Single transduced, fluorescent cells were sorted into individual wells of a 96-well plate. Two wells of the plate were seeded with 500 cells each, and were later combined as the "bulk" population. Cell colonies grew in 28 of the wells. These 28 clones were split into individual wells of 24-well plates in preparation for harvest of the medium once they were confluent. The clones matured in two phases; 21 reached confluency on day 1 and day 2 of the harvests, and the other 7 reached confluency on days 4, 5, and 6.

The harvested medium was used to infect D17 cells, and a primary screen was conducted by using flow cytometry essentially as described below, with an anti-AP antibody to determine what percentage of D17 cells had been infected. Briefly, the primary screen comprises plating D17 cells at $5 \times 10^4$ per well of 24 well plates on day 1. On day 2, the medium was replaced with fresh medium containing 4 µg/ml Polybrene, and exposed to 5 µl of test medium from each clone. On day 4, the cells were prepared for flow cytometry as described above except that the primary antibody was a mouse anti-human placental alkaline phosphatase from clone 8B6 and the secondary antibody was FITC-conjugated anti-mouse Fc (PharMingen, San Diego, Calif.). Based on the flow cytometry data, six clones were selected for the secondary screen which were strongly represented by late-maturing clones (Five of the seven late-maturing clones were selected, and only one (clone 14) of the 21 early-maturing clones were selected).

For the secondary screen the clones selected in the primary screen were plated at $2 \times 10^5$ cells per 3.5 cm diameter well of 6-well plates on day 1. On day 2, the medium was changed, and the virus-containing medium was harvested on day 3. D17 cells were infected with the medium from the clones and were stained for $AP^+$ foci to determine the LAPSN titers Table 3 shows that the best clone was determined to be PD223/LAPSN clone 14. For unknown reasons, the LAPSN titer produced by the "bulk" (sorted for AP expression but noncloned) PD223/LAPSN population was low in this experiment; in a repeated experiment, the LAPSN titer was found to be $6 \times 10^4$ AP+ FFU/ml per ml. The PD223/LAPSN c14 cells consistently produce a titer of $4 \times 10^5$ AP+ FFU/ml. Titers of up to $5 \times 10^5$ have been achieved in some experiments.

TABLE 3

Assay of Vector Production from PD223/LAPSN and PD223/LNCG Clones Obtained from Secondary Screens

| PD223/LAPSN clone | $AP^+$ FFU/ml |
|---|---|
| bulk | $6.9 \times 10^3$ |
| c1 | $5.1 \times 10^4$ |
| c3 | $1.0 \times 10^5$ |
| c6 | $9.1 \times 10^4$ |
| c7 | $1.4 \times 10^5$ |
| c14 | $4.3 \times 10^5$ |
| c20 | $2.0 \times 10^5$ |
| PD223/LNCG clone | $GFP^+$ FFU/ml |
| bulk | $1 \times 10^3$ |
| c10 | $8 \times 10^3$ |
| c11 | $1 \times 10^4$ |
| c14 | $2 \times 10^4$ |
| c24 | $2 \times 10^4$ |
| c30 | $1 \times 10^4$ |

Values are expressed as the mean of those obtained in duplicate assays in which each value varied from the mean by no more than 22% for the LAPSN titers and 13% for the LNCG titers.

PD223/LNCG cells were also cloned to obtain a high titer producer line of LNCG(PD223). The plasmid pLNCG was constructed by inserting the sequence encoding the green fluorescent protein (GFP) into the cloning site of plasmid pLNCX (Miller and Rosman, *BioTechniques* 7:980–990 (1989)). High titer producers were selected as described for the PD223/LAPSN clone, except that an antibody was not needed for the flow cytometry because LNCG encodes green flourescent protein. To create and select the best clone of PD223/LNCG, PD223 cells were plated at $10^5$ cells per 3.5 cm diameter well of 6-well dishes on day 1. On day 2, the medium was replaced with fresh medium containing 4 µg Polybrene per ml, and either 1 ml (MOI-1) or 100 µl (MOI~0.1) of LNCG(PT67)-containing medium was added.

The LNCG(PT67) stock had previously been found to have a titer of $2 \times 10^5$ $GFP^+$ FFU/ml. On day 4, the cells were prepared for FACS. Briefly, the cells were trypsinized, diluted in 2 ml phosphate buffered saline (PBS) containing 2% FBS, centrifuged at 1400 rpm for 5 min, and resuspended in 3 ml PBS containing 2% FBS and 1 µg/ml propidium iodide. The vector expresses Green Fluorescent Protein which provides a visible signal when excited by blue light of the appropriate wave length. Propidium iodide also added in this assay. The cells were sorted with a Becton Dickinson FACS VANTAGE Cell sorter equipped with an automated cell deposition unit (Becton Dickinson, San Jose, Calif.).

The cells were gated as described above and single GFP-positive cells sorted into individual wells of 96-well plates. Two bulk populations were also sorted, and later combined to yield the "bulk" population. Cells expressing GFP were sorted into wells of a 96-well plate and colonies were split into wells of a 24-well dish as they matured. For a primary screen, medium samples from 30 clones were harvested and used to infect D17 cells, and the percent infected was analyzed by flow cytometry. Five clones were selected for a secondary screen.

For a secondary screen, clones selected in the primary screen were plated at $2 \times 10^5$ cells per 3.5 cm diameter well of 6-well plates on day 1. On day 2, the medium was changed, and the virus-containing medium was harvested on day 3. D17 cells were infected with the medium from the clones and were observed under blue light to determine the LNCG titers. Table 3 shows that all selected clones packaged LNCG at a similar rate that was higher than that by the "bulk" (sorted for positive GFP expression but noncloned) population, and that two clones, clone 14 and clone 24, packaged LNCG at the highest rate.

Viral interference experiments were conducted to determine whether a vector packaged by the PD223 cells uses the same receptor as that used by MDEV (Table 4). Viral interference experiments rely on the observation that a cell that is producing a retroviral Env is resistant to infection by a retrovirus that uses the same receptor as the expressed Env. The entry of LAPSN(PD223) was dramatically impeded by the presence of MDEV that had been activated by hydrocortisone ($>2 \times 10^4$ fold inhibition), while the entry of LAPSN(PA317) was equivalent on both cell types. LAPSN (PD223) and LAPSN(PA317) contain the same Gag and Pol proteins, indicating that the inhibition was Env-specific and at the level of viral entry.

TABLE 4

Vectors Packaged by PD223 Cells Use the Same Receptor as MDEV

| LAPSN pseudotype | LAPSN Titer (FFU/ml) on | | Fold Interference |
|---|---|---|---|
| | *dunni*/N2 | *dunni*/N2 + MDEV | |
| PD223 | $6 \times 10^4$ | <2.5 | $>2 \times 10^4$ |
| PA317 | $1 \times 10^6$ | $1 \times 10^6$ | 1 |

The titer is expressed as the mean of duplicate assays in which each value varied by no more than 6% of the mean. The experiment was repeated with nearly identical results. The LAPSN(PD223) stocks had a titer of 3 x $10^5$ $AP^+$ FFU/ml on D17 cells. PA317 refers to a packaging cell line that pseudotypes vectors in the amphotropic MLV envelope.

A preferred packaging cell line is capable of packaging retroviral vectors without producing contaminating replication-competent retroviruses (RCR), or helper virus. $S^+L^-$ assays are often used to detect helper virus, but these were not used here because previous experiments have shown that wild-type MDEV does not score on $S^+L^-$ assays utilizing PG4 cells, CCC-81 cells overlaid with NRK cells, Mv1Lu cells, or SC-1 cells overlaid with Mv1Lu cells (Miller et al., *J. Virol.* 70:1804–1809 (1996)). To test whether the PD223 packaging cells produce helper or RCR, test medium harvested from PD223/LAPSN cells was placed on G355/LAPSN or dunni/LAPSN cells. The G355/LAPSN and dunni/LAPSN cells were passaged for more than two weeks, and then the medium was transferred to G355 or *M. dunni* cells. Test medium which contains RCR capable of replication on the cells package the LAPSN vector, allowing its detection on the final indicator cells. The same type of cells were used for the final indicator cells as the LAPSN-containing amplification cells to ensure that any amplified virus could infect the indicator cells. Two assays using different cell types were used to enhance the probability of detecting RCR.

The packaging cell medium was tested for RCR by first plating G355/LAPSN or dunni/LAPSN cells at $2\times10^5$ cells per 6 cm diameter dish in 3 ml of medium on day 1. On day 2, the test stock (packaging cell medium) was added in the presence of fresh medium containing 4 μg/ml of Polybrene. The cells were passaged in the presence of Polybrene to facilitate viral spread, during which time they were split 1:10 every several days. On day 17, the medium was harvested and titered on G355 cells for the G355 assay or *M. dunni* cells for the dunni assay. In all cases, the dunni cells had not been exposed to agents that activate the endogenous MDEV and so were not expressing MDEV. The LAPSN titer was determined on the final indicator cells as described previously. The titer ($AP^+$ FFU/ml) was expressed as the mean of those determined by duplicate assays in which each value varied from the mean by no more than 20% of the mean for the G355 assay and 4% of the mean for the dunni assay.

Table 5 shows that both the G355 and dunni assays were able to detect wild-type MDEV, and both assays can also efficiently detect amphotropic MLV. Neither assay, however, detected any RCR in the medium harvested from PD223/LAPSN cells.

TABLE 5

PD223 Cells do not Produce Detectable Replication-Competent Retrovirus

| Source of test medium | Vol. Medium added | G355 Assay Titer | dunni Assay Titer |
|---|---|---|---|
| PD223/LAPSN | 1 ml | <2 | <2 |
| PD223/LAPSN | 1 ml | <2 | <2 |
| G355/LAPSN + MDEV | 0.1 μl | $4 \times 10^4$ | $2 \times 10^4$ |
| G355/LAPSN + MDEV | 0.01 μl | $6 \times 10^3$ | <2 |
| no virus | 0 μl | <2 | <2 |

CHO cells are known to be difficult to transduce with retroviral vectors without pretreatment with tunicamycin, with a block at the level of viral entry (Miller and Miller, *J. Virol.* 65:78–84 (1992)). Previous data demonstrated that a vector pseudotyped by wild-type MDEV can efficiently transduce CHO cells, so the LAPSN vector packaged by PD223 cells was compared to LAPSN packaged by other packaging cells for the ability to transduce CHO cells (Table 6). CHO cells were plated at $1\times10^5$ cells per 3.5 cm diameter well of a 6-well dish on day 1, infected with the appropriate vector on day 2, and stained for $AP^+$ foci on day 4, as described above. Titers were expressed as the mean of those determined by duplicate assays, in which each value varied from the mean by no more than 18%. The titers of LAPSN packaged by the various cell lines were generally low on CHO cells, as predicted. However, the titer on permissive cells (D17 or NIH 3T3) was high for each stock, demonstrating that there was functional virus present that did not transduce the CHO cells. The most efficient entry into CHO cells was achieved by LAPSN(PD223).

TABLE 6

Vectors Packaged by PD223 Efficiently Transduce CHO Cells

| | | LAPSN Titer FFU/ml on: | | |
|---|---|---|---|---|
| Packaging Cells | Envelope | CHO | D17 | NIH 3T3 |
| PA317 | amphotropic | <20 | $1 \times 10^6$ | N.D. |
| PG13 | GALV | 600 | $3 \times 10^6$ | N.D. |
| PT67 | 10A1 | 800 | $3 \times 10^5$ | N.D. |
| PM571 | MCF/polytropic | <20 | N.D. | $1 \times 10^5$ |
| PE501 | ecotropic | <20 | N.D. | $1 \times 10^6$ |
| FLYRD | RD114 | <20 | $4 \times 10^6$ | N.D. |
| PD223 | MDEV | $2 \times 10^4$ | $2 \times 10^5$ | N.D. |
| wild-type MDEV | MDEV | $8 \times 10^4$ | $7 \times 10^4$ | N.D. |

EXAMPLE IV

Retroviral Receptors for Entry into *M. dunni* Cells

This example describes at least six different receptors used by murine retroviruses for entry into *M. dunni* cells. Pseudotypes of a retroviral vector encoding human placental alkaline phosphatase (AP) was used to determine interference in *M. dunni* cells. Using this direct assay, interference patterns in *M. dunni* cells were found to be similar to those reported for other cells, indicating that murine retroviruses use at least six different receptors for entry into *M. dunni* cells.

The following replication-competent retroviruses were used in interference assays described in more detail below: 1387, MoMLV strain 1387; AKR623, AKR MLV strain 623; 1E, Friend MCF strain 1E; 4070A and 1504A, amphotropic MLV strains 4070A and 1504A (Chesebro and Wehrly *Virol.* 141:119–129 (1985)). The MLV-K strain of MoMLV was obtained from NIH 3T3 cells transfected with the pMLV-K clone of MoMLV (Miller and Verma, *J. Virol.* 49:214–222 (1984)). NZB xenotropic virus was obtained from *M. dunni* cells transfected with the circularly permuted NZB molecular clone NZB 9-1 (O'Neill et al., *J. Virol.* 53:100–106 (1985)) after cutting the plasmid with Eco RI and religating the DNA to generate intact NZB provirus circles. 10A1 virus was obtained from NIH 3T3 cells transfected with the permuted 10A1 virus DNA clone pB6 (Ott et al., *J. Virol.* 64:757–765 (1990)) after cutting the plasmid with Sal I and religating the DNA to generate intact 10A1 provirus circles. The LN retroviral vector encodes neomycin phosphotransferase (Miller and Rosman, *BioTechniques* 7:980–990 (1989)), and the LAPSN vector encodes neomycin phosphotransferase and human placental alkaline phosphatase (AP) (Miller et al., *Proc. Natl. Acad. Sci. U.S.A.* 91:78–82 (1994)).

For the assays, *M. dunni* tail fibroblasts (dunni cells) (Lander and Chattopadhyay, *J. Virol.* 52:695–698 (1984)) were grown in Dulbecco's modified Eagle's medium with 4.5 g/l glucose and 5% fetal bovine serum at 37° C. in a 10% $CO_2$/air atmosphere. PE501 ecotropic, PM571 polytropic, and PA317 amphotropic retrovirus packaging cell lines were grown under similar conditions except that 10% fetal bovine serum was used. dunni/LN and dunni/LAPSN cells were made by transduction with helper-free vector stocks produced by PA317 retrovirus packaging cells containing the vectors. The transduced cells were selected in G418 to ensure that all cells expressed the vectors. dunni/LN and dunni/LAPSN cells were infected with replication-competent viruses by seeding the cells the day before infection at $10^5$ per 6 cm dish, infecting the cells with 100 µl virus stock in the presence of 4 µg/ml Polybrene (Sigma), and passaging the cells for $\geq 11$ days in the absence of Polybrene to allow complete virus spread. Virus was harvested from confluent layers of cells 16 h after a medium change and frozen at $-70°$ C. Helper-free retroviral vectors were generated from retrovirus packaging cells as previously described (Miller and Rosman, *BioTechniques* 7:980–990 (1989); incorporated herein by reference in its entirety). The envelope protein in PE501 cells is from MoMLV molecular clone pMLV-K, that in PM571 is from Friend MCF strain 98D, and that in PA317 cells is from amphotropic MLV strain 4070A. Chesebro and Wehrly (*Virol.* 141:119–129 (1985); incorporated herein by reference) previously assigned viruses to different interference groups which exhibited interference in *M. dunni* cells. Their results can briefly be summarized as demonstrating that ecotropic virus 1387, but not ecotropic virus AKR623, interfered with polytropic viruses 98D and 1512, and both ecotropic viruses interfered with infection by xenotropic virus AKR6. Amphotropic virus 4070A, but not amphotropic virus 1504A, interfered with xenotropic virus AKR6 and ecotropic virus 1387 and with xenotropic virus AKR6. Polytropic virus 1E interfered with ecotropic virus 1387. Challenge by amphotropic viruses was not analyzed because amphotropic virus-specific antibodies were not available for virus detection in the immunofluorescence assay used.

The *M. dunni* tail fibroblasts used previously (Chesebro and Wehrly, supra.), were obtained and transduced with the LN retroviral vector (Miller and Rosman, supra.), that expresses neomycin phosphotransferase, or with the LAPSN vector (Miller et al., supra. 1994), that expresses neomycin phosphotransferase and human placental alkaline phosphatase (AP), by using helper virus-free vector stocks made from PA317 retrovirus packaging cells (Miller and Buttimore, *Mol. Cell. Biol.* 6:2895–2902 (1986)) containing the vectors. The dunni/LN and dunni/LAPSN cells did not produce the vectors in the absence of added replication-competent virus. The original retroviruses used previously (Chesebro and Wehrly, supra.) were obtained and used to infect the dunni/LN and dunni/LAPSN cells. The presence of replication-competent retrovirus was confirmed in all cases by measurement of the production of the LN or LAPSN vectors. Interference assays were performed by first seeding infected (dunni/LN cells infected with the interfering virus) and uninfected dunni/LN cells at $5 \times 10^4$ per 3 cm-diameter well of 6-well culture trays on day one. On day two, the medium was replaced with 2 ml medium containing 4 µg/ml Polybrene and the challenge pseudotyped LAPSN vectors. On day 4, the cells were stained for alkaline phosphatase-positive foci as described (Fields-Berry et al., *Proc. Natl. Acad. Sci. U.S.A.* 89:693–697 (1992). Transduction (gene transfer and expression) by the LAPSN vector was measured by staining for foci of alkaline phosphatase-positive cells. Results were expressed as the $\log_{10}$ of the fold interference, or $\log_{10}$ [(LAPSN vector titer on uninfected dunni/LN cells)/(LAPSN vector titer on dunni/LN cells infected with the interfering virus)]. The presence of the LN vector in the target cells did not interfere with transduction by the LAPSN vector or with detection of AP expression, and was only included to allow detection of the presence of the interfering viruses by measurement of LN vector production.

The results of the present interference analysis (Table 7) were inconsistent with the prior results obtained in *M. dunni* cells by Chesebro and Wehrly, summarized above, but were consistent with previously determined interference groupings in other cell types. Interference between viruses in the same group ranged from 20- to 300,000-fold, while interference between viruses from different groups was less than or equal to 10-fold. Disregarding the results obtained when the interfering virus was 1387 (discussed below), and the results showing partial interference between polytropic and xenotropic viruses (Cloyd et al., *Virol.* 140: 239–248 (1985); work in other than *M. dunni* cells), the difference between intragroup interference (160- to 300,000-fold) and intergroup interference (less than or equal to 2-fold) is even more dramatic.

TABLE 7

Interference of MLV in *M. dunni* Cells Measured by Marker Transfer Assay[a]

| LAPSN Pseudo-type | Vector Titer log (FFU/ml) | Result with Interfering MLV | | | | |
|---|---|---|---|---|---|---|
| | | Ecotropic | | Polytropic | Amphotrophic | |
| | | 1398 | AKR623 | 1E | 4070A | 1504A |
| Ecotropic | | | | | | |
| 1387 | 6.0 | 1.4 | 2.5 | 0.0 | 0.0 | 0.1 |
| PE501 | 4.1 | 1.3 | >3.6 | 0.2 | 0.3 | 0.0 |
| Polytropic | | | | | | |
| 1E | 7.0 | 0.3 | ND[b] | 4.6 | ND | ND |
| PM571 | 5.0 | 0.7 | 0.0 | 2.2 | 0.0 | 0.0 |
| 1512 | 5.5 | 0.6 | 0.0 | 5.5 | ND | ND |
| Xenotropic | | | | | | |
| AKR6 | 6.8 | 0.5 | 0.2 | 1.0 | 0.2 | 0.2 |
| NZB | 6.7 | 0.5 | 0.1 | 1.0 | 0.1 | 0.2 |
| Amphotropic | | | | | | |
| 4070A | 6.8 | ND | ND | ND | 5.2 | 4.4 |
| PA317 | 6.3 | 0.4 | 0.1 | 0.1 | 5.4 | 4.5 |
| 1504A | 7.0 | ND | ND | ND | 3.0 | 3.0 |

[a]The LAPSN vector with the indicated pseudotypes was used to infect dunni/LN cells or dunni/LN cells infected with the indicated interfering MLVs, and the apparent vector titers in FFU/ml were determined. The vector titer is expressed in the Table as the $\log_{10}$ of the mean titer determined on dunni/LN cells, and is an arithmetic mean of at least two experiments. Interference values are expressed as the $\log_{10}$ of the fold interference, or $\log_{10}$ (LAPSN titer on uninfected dunni/LN cells)/(LAPSN titer on dunni/LN cells infected with the interfering virus). The fold interference was calculated as the arithmetic mean of at least two independent determinations, which varied by no more than 58% from the mean. Boxed areas indicate interference between viruses in the same interference group.
[b]Not determined.

Interference analyses with additional pseudotypes of the LAPSN vector confirmed the interference group assignments of the replication-competent viruses used in the previous study (Table 7). LAPSN virus produced by PE501 ecotropic packaging cells behaved like the ecotropic LAPSN (1387) virus. PE501 cells were constructed by using the pMLV-K clone of MoMLV (Miller and Verma, *J. Virol.* 49:214–222 (1984)), and 1387 virus represents a different isolate of MoMLV. LAPSN produced by PM571 Friend MCF strain 98D-based packaging cells (Miller and Miller, *J. Virol.* 66:78–84 (1992)) behaved like the other polytropic-pseudotype LAPSN vectors, although the interference observed for LAPSN(PM571) in *M. dunni* cells infected with 1E virus was not as great as observed for the other polytropic viruses. LAPSN pseudotyped with the xenotropic NZB virus (O'Neill et al., *J. Virol.* 53:100–106 (1985)) behaved like the xenotropic AKR6 pseudotype. LAPSN (PA317) behaved like the other amphotropic pseudotypes of the vector, but the best correlation was with LAPSN (4070A), which was expected since PA317 cells were constructed by using env from a molecular clone of 4070A.

The results obtained when the interfering virus was 1387 were somewhat anomalous. The 1387 virus-infected dunni/LN cells grew slowly, displayed many multinucleated cells, and exhibited high rates of cell death, a phenomenon that persisted even with prolonged cultivation. Infection rates observed for non-ecotropic LAPSN pseudotypes in 1387 virus-infected dunni/LN cells were low compared to those obtained in uninfected dunni/LN cells is most likely due to cell death and slow growth of the 1387 virus-infected dunni/LN cells rather than interference by the 1387 virus. In addition, the continued presence of multinucleated cells in the dunni/LN cells infected with 1387 virus indicates that the receptor used by 1387 virus is not effectively blocked by the virus, resulting in continued virus-mediated cell fusion, and provides an explanation for the poor interference of the 1387 virus with ecotropic pseudotype LAPSN viruses.

To test whether the behavior of *M. dunni* cells infected with 1387 virus was a peculiar property of this strain of MoMLV, or perhaps was due to a contaminating virus present in the virus preparation, *M. dunni* cells were infected in parallel with 1387 virus harvested from 1387 virus-infected dunni/LAPSN cells, or with virus harvested from NIH 3T3 cells transfected with a DNA clone of MoMLV, pMLV-K (Miller and Verma, supra.), and the cells were observed during several passages in culture. The presence of large multinucleated cells that increased in number with time was observed in *M. dunni* cells infected with either virus preparation, although it was most pronounced in cells infected with 1387 virus. These results indicate that the toxicity and cell fusion observed in 1387 virus-infected *M. dunni* cells is not due to a contaminant in the 1387 virus stock, but is typical of MoMLV infection in *M. dunni* cells.

Others have found that *M. dunni* tail fibroblasts are poorly infected by MoMLV and by vectors with an MoMLV pseudotype, even though these cells can be efficiently infected by other ecotropic viruses (Eiden et al., *J. Virol.* 67:4056–4061 (1993); Eiden et al., *J. Virol.* 68:626–631 (1994); Lander and Chattopadhyay, *J. Virol.* 52:695–698 (1984)). In contrast, the present study found that *M. dunni* cells were relatively efficiently infected by the LAPSN vector with a 1387 (MoMLV) pseudotype, the apparent titer on *M. dunni* cells being $10^6$ FFU/ml (Table 7). There are two types of *M. dunni* tail fibroblasts in common use, and the use of different cells by different labs might explain the these results. The type used here can be recognized by the unusual characteristic that confluent layers of the cells secrete molecules that render the culture medium highly viscous, a property that is not shared with the *M. dunni* cells used in other studies (Eiden et al., supra., 1993 and Eiden et al., supra., 1994). The strains used herein are referred to as dunni-v and dunni-nv (to denote viscous and non-viscous medium, respectively).

Dunni-nv cells (Eiden et al. (1993), supra.) were directly compared with the dunni-v cells (Table 8). The apparent titer of the PESO (MoMLV) pseudotype LAPSN vector was similar in both dunni cell strains, but was up to 250-fold lower in dunni cells as compared with NIH 3T3 cells. The titer of the 1387 (MoMLV) pseudotype LAPSN vector was also similar on both dunni cell strains, but was reduced by only about 6-fold in dunni cells compared with NIH 3T3 cells. For comparison, the titer of amphotropic LAPSN vector was similar in both *M. dunni* cell strains and in NIH 3T3 cells. The ecotropic virus AKR623, which is not an MoMLV strain, promoted LAPSN infection of dunni-nv cells at the same rate as NIH 3T3 mouse cells, but at a 20-fold lower rate in dunni-v cells. Thus, while there are virus strain- and cell strain-dependent variations in ecotropic-pseudotype vector infection of *M. dunni* cells, both *M. dunni* cell lines can be infected by virions carrying the MoMLV envelope. The markedly lower rate of infection in *M. dunni* cells in comparison to NIH 3T3 cells seen for one strain of MoMLV is consistent with prior observations (Eiden et al., supra. (1993); Eiden et al., supra. (1994); Lander and Chattopadhyay, supra. (1984)).

TABLE 8

Ecotropic Vector Titers Measured on *M. dunni* Cells from Different Sources

| LASPN Pseudotype Strain | Expt | Titer (FFU/ml) on cell line: dunni-v | dunni-nv | NIH-3T3 |
|---|---|---|---|---|
| Ecotropic | 1 | $5 \times 10^3$ | $3 \times 10^3$ | ND[b] |
| PE501 | 2 | $3 \times 10^4$ | $4 \times 10^3$ | $1 \times 10^6$ |
| 1387 | 1 | $6 \times 10^5$ | $4 \times 10^5$ | ND |
|  | 2 | $1 \times 10^6$ | $5 \times 10^5$ | $4 \times 10^6$ |
| AKR623 | 1 | $2 \times 10^4$ | $6 \times 10^5$ | ND |
|  | 2 | $2 \times 10^4$ | $3 \times 10^5$ | $4 \times 10^5$ |
| Amphotrophic | 2 | $5 \times 10^5$ | $1 \times 10^6$ | $1 \times 10^6$ |
| PA317 | 1 | $2 \times 10^6$ | $3 \times 10^6$ | ND |

[a]Cells were seeded at $10^5$ per 3 cm-diameter well of 6 well culture trays one day prior to infection and stained for alkaline phosphatase-positive foci as described previously (Fields-Berry, supra.) two days after infection. Each value is the mean of duplicate assays which varied by no more than 27% from the mean.
[b]ND, not determined.

The dunni-v cells are most likely derived from *M. dunni* animals, and are not cells from another species due to culture contamination or mistaken identification. This conclusion depends on Southern analyses of restriction enzyme-digested DNA samples from these *M. dunni* cells and from *M. dunni* mice, which show identical patterns of bands that hybridize to a probe made from the relatively unique endogenous virus MDEV, while DNA samples from cell lines derived from laboratory mice show a different pattern of weakly-hybridizing bands, and DNA samples from cells of other species show no hybridization (Example I). Southern analyses also show similar patterns of bands that hybridized to an MDEV probe for DNA from dunni-nv and dunni-v cells, indicating both cell types are of similar origin, and thus that both lines were likely from *M. dunni* mice. The different phenotypes of the two *M. dunni* cell strains may be due to the fact that the original isolate (Lander and Chattopadhyay, supra., (1984)) was not cloned before distribution, and it appears that different culture conditions may have permitted outgrowth of different subpopulations of *M. dunni* cells.

Finally, interference between representatives of all of the MLV interference groups was examined in *M. dunni* (dunni-v) cells (Table 9). Ecotropic and MDEV viruses showed no interference with any of the other groups. 10A1 and amphotropic viruses showed nonreciprocal interference, but no interference with any of the other groups. Similarly, polytropic and xenotropic groups showed nonreciprocal interference, but no interference with any other groups. The reason for the more complicated interference patterns previously observed among these groups in *M. dunni* cells (Chesebro and Wehrly, supra.) is likely due to the assay employed, which required spread of the challenge virus after infection to produce a signal, and virus spread might have been inhibited by the interfering virus. Alternatively, detection of the challenge virus with antibodies may have been difficult due to background staining of the interfering virus that was present in all cells. The assay used here more directly measures virus entry and does not require virus spread. The present results did not show altered receptor utilization or altered coreceptor usage in *M. dunni* cells. Thus, murine retroviruses can be divided into six interference groups that use at least six different receptors for entry into *M. dunni* cells.

der carcinoma cells (ATCC HTB 9), transformed human airway epithelial cell line, IB3 cells (Zeitlin et al., *Am. J. Respir. Cell Mol. Biol.* 4:313–319 (1991)), HT1080 cells (ATCC CCL 121), NRK cells (DeLarco, et al., *J. Cell Physiol.* 94:335–342 (1978)), and Balb/c 3T3 (B77/OTG) ouabain resistant HPRT⁻ cells transformed by Rous sarcoma virus were grown in Dulbecco's modified Eagle's medium (DMEM) with 4.5 g glucose per liter and 10% fetal bovine serum (FBS), primary human dermal fibroblasts (HDF) (Halbert et al., *J. Virol.* 69:1473–1479 (1995)) were grown in DMEM with 15% FBS, respectively. G355 feline embryonic glial cells and G355 cells infected with RD114 endogenous cat virus (Dunn et al., supra.) were grown as described in Example 1. CHO-K1 cells (ATCC CCL 61) were grown in αMEM with 10% FBS. HUT 78 cells (ATCC TIB 161) were grown in RPMI 1640 plus 10% FBS. QT35 cells (Moscovici et al., *Cell* 11:95–103 (1977)) were grown in

TABLE 9

Interference of Representatives of Six Murine Leukemia virus Groups in *M. dunni* Cells[a]

| LAPSN Pseudotype (strain) | Vector Titer log (FFU/ml) | Result with Interfering MLV Group (strain) | | | | | |
|---|---|---|---|---|---|---|---|
| | | Ecotropic (AKR623) | Polytropic (IE) | Xenotropic (NZB) | Amphotropic (4070A) | 10A1 (10A1) | MDEV (MDEV) |
| Ecotropic, (PE501) | 3.8 ± 0.1 | >3.6 | — | — | — | — | — |
| Polytropic, (1E) | 7.1 ± 0.1 | — | 5.5 ± 1.0 | 5.9 ± 0.4 | — | — | — |
| Xenotropic, (AKR6) | 6.7 ± 0.1 | — | 1.0 ± 0.3 | 6.0 ± 0.5 | — | — | — |
| Amphotropic (PA317) | 6.0 ± 0.4 | — | — | — | 5.6 ± 0.1 | 5.9 ± 0.3 | — |
| 10A1, (PT67) | 6.3 ± 0.1 | — | — | — | 0.8 ± 0.0 | 6.3 ± 0.1 | — |
| MDEV (MDEV) | 6.0 ± 0.1 | — | — | — | — | — | 5.5 ± 0.8 |

[a]The LAPSN vector with the indicated pseudotypes was used to infect *dunni*/LN cells or *dunni*/LN cells infected with the indicated interfering MLVs, and the apparent vector titers in FFU/ml were determined. The vector titer is indicated in the Table as the $log_{10}$ of the mean titer determined on *dunni*/LN cells, and is an arithmetic mean of at least two experiments. Interference values are expressed as the $log_{10}$ of the fold interference, or $log_{10}$ (LAPSN titer on uninfected *dunni*/LN cells)/(LAPSN titer on *dunni*/LN cells infected with the interfering virus) The fold interference was calculated as the arithmetic mean of at least two independent determinations, which varied by no more than 58% from the mean.

EXAMPLE V

Characterization of the MDEV Interference Group and Host Range

MDEV was activated from the cells of the Asian wild mouse during testing of human cells for replication-competent virus in human gene transfer trials (Miller et al. *J. Virol.* 70:1804–1809 (1996)). MDEV did not appear to match the descriptions of previously known viruses and was shown to use a unique receptor and does not belong to any of the murine retrovirus interference groups (Example IV). This Example describes tests for interference between MDEV and viruses from additional interference groups.

To characterize the MDEV interference group and host range the following cells and conditions were applied. *M. dunni* tail fibroblasts (Chattopadhyay et al., *Virology* 113:465–483 (1981)), PA317 amphotropic retrovirus packaging cells, PG13 gibbon ape leukemia virus (GALV)-based packaging cells, NIH 3T3 thymidine kinase-negative cells (Miller et al., *Mol. Cell. Biol.* 6:2895–2902 (1986)), C2C12 cells (ATCC CRL 1772), HeLa cells (ATCC CCL 2), D17 cells (ATCC CCL 183), CCC-81 cat cells transformed with Moloney murine sarcoma virus (Fischinger et al., *Proc. Natl. Acad. Sci. U.S.A.* 72:5150–5155 (1975)), 5637 human blad- Ham's F10 medium with 10% tryptose phosphate broth, 1% chick serum, 1% DMSO, 5% FBS, and 2% sodium bicarbonate (7.5% solution). LAPSN infection was scored by histochemical staining for AP+ foci of cells two days after infection as described (Miller and Chen., *J. Virol.* 70:5564–5571 (1996); incorporated herein by reference in its entirety).

The replication competent viruses used in this Example included ecotropic Moloney murine leukemia virus (MoMLV) (pMLV-K; Miller and Verma, (1984) supra.), amphotropic virus (AM-MLV; Miller et al., *Mol. Cell. Biol.* 6:2895–2902 (1986)), NZB xenotropic (O'Neill et al., *J. Virol.* 53:100–106 (1985)), polytropic (MCF) virus strain 98D (Chesebro and Wehrly, (1985) supra.), 10A1 (Ott et al., (1990) supra.), gibbon ape leukemia virus (GALV) SEATO strain (Wilson et al., *J. Virol.* 63:2374–2378 (1989)), RD114 (Reeves et al., *J. Virol.* 52:164–171 (1984)), and *M. dunni* endogenous virus (MDEV) (Miller et al. (1996) supra.). Additional viral elements used in proviral DNA form in hybridization studies include: mouse mammary tumor virus (MMTV) (Shackleford and Varmus, *Proc. Natl. Acad. Sci. U.S.A.* 85:9655–9659 (1988)), GALV envelope (Wilson et al., (1989) supra.), and human endogenous retroviral elements (HERV-K) (Lower et al., *Proc. Natl. Acad. Sci. U.S.A.* 90:4480–4484 (1993)) and HERV-H (Wilkinson et al., *J.*

Virol. 64:2157–2167 (1990)). D17 cells infected with spleen necrosis virus (SNV) or Mason Pfizer monkey virus (MPMV) were also used. SNV-infected D17 cells were made by infection of D17 cells with SNV followed by cultivation of the cells to allow virus spread to all cells. MPMV-infected D17 cells were made by cocultivation of D17 cells with MPMV-producing human CEM cells to compensate for the poor infectivity of MPMV for D17 cells. SNV-pseudotype LAPSN vector was made by infecting D17/SNV cells with helper-free amphotropic LAPSN vector produced from PA317 cells, selecting the cells in G418, growing the G418-resistant cells in the absence of G418, and harvesting virus from confluent dishes of cells about 16 h after a medium change. RD114-pseudotype LAPSN vector was made in a similar manner following infection of G355/RD114 cells with the helper-free LAPSN vector.

MDEV is not in the GALV or RD114 retrovirus interference groups, and MDEV uses a different receptor for entry than those used by other murine leukemia viruses by interference analysis (Table 9, Miller et al., (1996) supra.). Tests for interference between MDEV and viruses from additional groups including the gibbon ape leukemia virus (GALV) and the RD114 cat endogenous virus groups were carried out. These viruses were chosen because members of the GALV interference group have been found to interfere with an endogenous retrovirus from the Asian mouse *M. caroli* (Callahan et al., p.689–713. In H. C. Morse III (ed.), *Workshop on the origins of inbred mice,* Academic Press, Inc., New York (1978); Lieber et al., Proc. Natl. Acad. Sci. U.S.A. 72:2315–2319 (1975)), and some interference between RD114 and MDEV in cat cells has been observed (Miller et al., (1996) supra.). Interference analysis in primary human dermal fibroblasts (HDF) (Table 10) showed that cells infected with MDEV inhibited transduction by MDEV-pseudotype LAPSN vector by about 100-fold, but did not inhibit transduction by LAPSN with either a GALV, amphotropic, or RD114 pseudotype. Similarly, prior infection of the cells with GALV, 10A1, or RD114 virus inhibited entry inhibited entry by LAPSN virus having GALV, amphotropic, or RD114 pseudotypes, respectively, by 100- to almost 100,000-fold, but had no effect on transduction by LAPSN virus with a different pseudotype. Note that 10A1 virus is essentially an amphotropic virus in these human cells (Miller and Chen, *J. Virol.* 70:5564–5571 (1996)). Thus, MDEV, GALV, 10A1, an amphotropic virus, and RD114 virus are in different interference groups when assayed in human cells, indicating that these virus groups use different receptors for cell entry.

TABLE 10

Interference Properties of MDEV, GALV, Amphotropic Virus, 10A1, and RD114 Measured in Human Diploid Fibroblasts[a]

| Interfering Virus | LAPSN Titer for the Following Pseudotypes: | | | |
|---|---|---|---|---|
| | MDEV | PG13[b] | PA317[c] | RD114 |
| none | $3 \times 10^4$ | $3 \times 10^5$ | $9 \times 10^4$ | $5 \times 10^5$ |
| MDEV | 200 | $5 \times 10^5$ | $6 \times 10^4$ | $5 \times 10^5$ |
| GALV | $2 \times 10^4$ | 200 | $4 \times 10^4$ | $2 \times 10^5$ |

TABLE 10-continued

Interference Properties of MDEV, GALV, Amphotropic Virus, 10A1, and RD114 Measured in Human Diploid Fibroblasts[a]

| Interfering Virus | LAPSN Titer for the Following Pseudotypes: | | | |
|---|---|---|---|---|
| | MDEV | PG13[b] | PA317[c] | RD114 |
| 10A1 | $5 \times 10^4$ | $9 \times 10^4$ | 1 | $2 \times 10^5$ |
| RD114 | $4 \times 10^4$ | $8 \times 10^4$ | $1 \times 10^5$ | $2 \times 10^3$ |

[a]Uninfected HDF cells and HDF cells infected with the indicated interfering viruses were exposed to LAPSN vectors with the indicated pseudotypes and were stained for AP+ foci of cells two days after infection. Values are means of duplicate assays in a single experiment which varied by no more than 33% from the mean (except for the value 1, which represents the mean of 0 and 2 FFU/ml). The experiment was repeated with similar results.
[b]PG13 refers to a packaging cell line which produces GALV-pseudotype virus.
[c]PA317 refers to a packaging cell line which produces amphotropic-pseudotype virus.

Because MDEV-pseudotype vectors appeared to infect feline CCC-81 cells poorly, and cat cells contain and could potentially express the cat endogenous virus RD114, interference between MDEV and RD114 was also tested in G355 feline embryonic cells that are permissive for MDEV infection. In this case, prior infection of the G355 cells with RD114 inhibited transduction by the MDEV-pseudotype LAPSN vector by 5- to 500-fold (Table 11).

TABLE 11

RD114 Interferes with Transduction by a Vector Having an MDEV Pseudotype in G355 Cat Cells[a]

| Interfering Virus | LAPSN Titer for the Following Pseudotypes: | | |
|---|---|---|---|
| | RD114 | MDEV | PA317 |
| None | $2 \times 10^5$ | $2 \times 10^3$ | $6 \times 10^5$ |
| RD114 | 3 | 90 | $5 \times 10^5$ |

[a]G355 or RD114-infected G355 cat cells were exposed to LAPSN vectors with the indicated pseudotypes and were stained for AP+ foci of cells two days after infection. Results are means of at least two independent determinations, which varied by no more than 67% from the mean, except for the LAPSN(MDEV) infection of G355/RD114 cells, where the LAPSN titer varied from <2 to 300 FFU/ml (n = 6, mean = 90).

Table 11 shows the results of additional interference assays performed in D17 canine cells using additional representatives of the RD114 interference group. Prior infection of D17 cells with RD114, spleen necrosis virus (SNV), or Mason Pfizer monkey virus (MPMV; also called SRV-3) did not interfere with transduction by an MDEV-pseudotype LAPSN vector, but all three viruses interfered with transduction by LAPSN with an RD114 or an SNV pseudotype. These results are consistent with previous findings that RD114, SNV, and MPMV are in the same interference group when assayed in canine and human cells (Kewalramani et al., *J. Virol.* 66:3026–3031 (1992); Koo et al., *J. Virol.* 66:3448–3454 (1992), Sommerfelt et al., *Virology* 176:58–69 (1990)), and show that MDEV is in a different interference group when assayed in canine cells. It was not possible to examine transduction by MPMV-pseudotype LAPSN vector in this experiment because this type D virus did not package the MoMLV-based LAPSN vector (Takeuchi et al., *Virology* 186:792–794 (1992)).

TABLE 12

RD114, SNV and MPMV do not Interfere with Transduction by a
Vector Having an MDEV Pseudotype in D17 Dog Cells[a]

| Interfering Virus | LAPSN titer for the following pseudotypes: | | |
|---|---|---|---|
| | RD114 | SNV | MDEV |
| none | $3 \times 10^5$ | $5 \times 10^3$ | $4 \times 10^4$ |
| RD114 | 20 | 20 | $2 \times 10^4$ |
| SNV | $6 \times 10^4$ | 4 | $2 \times 10^4$ |
| MPMV | $2 \times 10^4$ | 20 | $2 \times 10^4$ |

[a]Uninfected D17 cells and D17 cells infected with the indicated interfering viruses were exposed to LAPSN vectors with the indicated pseudotypes and were stained for AP+ foci of cells two days after infection. Results are means of at least two independent determinations, which varied by no more than 60% from the mean.

These results show that MDEV is in a different interference group from those of GALV, amphotropic virus, 10A1, and RD114, although there appears to be some overlap for receptor utilization with the RD114 group in G355 cells. These findings extend results showing MDEV does not belong to the ecotropic, xenotropic, amphotropic, 10A1, or polytropic interference groups (Miller et al. (1996), supra. and Example IV).

MDEV has a wide host range, and MDEV-pseudotyped LAPSN virus was able to infect a variety of cell types from all species tested, including mouse, rat, hamster, quail, cat, dog and human cells (Table 13). The titer of LAPSN (MDEV) was between $10^5$ and $5 \times 10^6$ on all cells tested, except for Balb/c 3T3 cells, for which the titer was only 200 FFU/ml. No phenotypic changes were observed in cells infected with MDEV except in experiments with the HUT 78 human T cell line, in which an increase in doubling time and very large multinucleated cells were observed. The ability of MDEV-pseudotype vector to infect different cell types from multiple species indicates that the receptor used by this virus is widely distributed.

TABLE 13

Host Range of MDEV[a]

| LAPSN(MDEV) Species | Cell Type | Titer |
|---|---|---|
| Mouse (wild) | Mus dunni | $4 \times 10^5$ |
| Mouse (laboratory) | NIH 3T3 | $6 \times 10^5$ |
| | Balb/c 3T3 | 200 |
| | C2C12 | $1 \times 10^5$ |
| Rat | NRK | $2 \times 10^5$ |
| Hamster | CHO-K1 | $5 \times 10^6$ |
| Quail | QT35 | $8 \times 10^5$ |
| Cat | CCC-81 | $5 \times 10^5$ |
| | G355 | $4 \times 10^6$ |
| Dog | D17 | $2 \times 10^6$ |
| Human | HT1080 | $5 \times 10^6$ |
| | IB3 | $4 \times 10^6$ |
| | 5637 (HTB-9) | $5 \times 10^5$ |
| | HDF | $9 \times 10^5$ |
| | HeLa[b] | $5 \times 10^5$ |

[a]The indicated cells were exposed to MDEV-pseudotype LAPSN and were stained for AP+ foci of cells two days after infection. Values are means of duplicate assays in a single experiment which varied by no more than 25% from the mean. The experiment was repeated with similar results.
[b]The LAPSN(MDEV) titer on HeLa cells was measured by production of G418-resistant colonies (CFU/ml) rather than AP+ foci because HeLa cells have very high levels of endogenous alkaline phosphatase.

A virus produced from laboratory mouse-derived cell lines by activation with IdU is distinct from MDEV. NIH 3T3, C2C12, and Balb/c 3T3 laboratory mouse cells were exposed to either IdU or hydrocortisone. To activate endogenous virus, Balb/c 3T3, NIH 3T3, or C2C12 cells were seeded in 6-well plates at $4 \times 10^5$ cells per 3.5 cm-diameter well on day one. On day two, duplicate wells were treated with culture medium saturated with 5-iodo-2'deoxyuridine (IdU), medium containing 90 $\mu$M hydrocortisone 21-phosphate (Sigma), or medium alone for 24 h. On day three, the cells were trypsinized and co-cultivated with D17/LAPSN cells to allow for replication of viruses that might be unable to replicate in the mouse cells, and to allow detection of replication-competent retroviruses by measurement of LAPSN vector production. At weekly intervals following IdU treatment, medium exposed to the cell mixtures for 24 h was collected, filtered (0.45 $\mu$m pore size), and tested for the presence of LAPSN on M. dunni cells. The exposed cells were then cocultivated with D17/LAPSN cells to allow for replication of viruses that might be unable to replicate in the mouse cells, and to allow detection of replication-competent retroviruses by measurement of LAPSN vector production. Beginning at one week, duplicate wells of Balb/c 3T3 cells treated with IdU were found to be positive for production of LAPSN. The replication-competent virus that was activated is referred to herein as Balb/c 3T3 IdU-induced retrovirus (BIRV). Duplicate wells of Balb/c 3T3 cells which were treated with hydrocortisone or were untreated remained negative for the production of virus for the seven week duration of the experiment. In addition, replication-competent virus could not be detected after identical treatment of either NIH 3T3 or C2C12 cells.

Interference assay results showed that MDEV does not interfere with transduction by LAPSN(BIRV), but that both polytropic and xenotropic viruses do interfere with LAPSN (BIRV) (Table 14). These results indicate that BIRV is not in the same interference group as MDEV, but is a member of either the polytropic or xenotropic group of viruses, which are closely related and have been shown to interfere with each other in some cell types (Chesebro and Wehrly, supra., (1985)). The strains of polytropic and xenotropic virus used here show some degree of nonreciprocal interference in M. dunni cells, in that xenotropic virus strongly inhibits polytropic vector transduction ($10^5$-fold), while polytropic virus much less severely inhibits transduction by xenotropic virus (~40-fold). BIRV is capable of infecting M. dunni, NIH 3T3, G355, and primary human fibroblasts (Table 15), indicating that BIRV is a polytropic virus, since xenotropic viruses do not infect cells from laboratory mice.

TABLE 14

Endogenous Virus Induced from Balb/c 3T3 Cells
Uses a Different Receptor than MDEV in M. dunni cells[a]

| Interfering Virus | LAPSN Titer for the Following Pseudotypes: | | | |
|---|---|---|---|---|
| | MDEV | BIRV | Polytropic | Xenotropic |
| None | $6 \times 10^5$ | $8 \times 10^4$ | $1 \times 10^5$ | $4 \times 10^6$ |
| MDEV | 3 | $6 \times 10^4$ | ND[b] | ND |
| Polytropic | $4 \times 10^5$ | 400 | <1 | $1 \times 10^5$ |
| Xenotropic | $4 \times 10^5$ | <2 | 1 | 6 |
| Amphotropic | $4 \times 10^5$ | $5 \times 10^4$ | ND | ND |

[a]Uninfected M. dunni cells and M. dunni cells infected with the indicated interfering viruses were exposed to LAPSN vectors with the indicated pseudotypes and were stained for AP+ foci of cells two days after infection. Values are means of duplicate assays in a single experiment which varied by no more than 17% from the mean (except for the value 3 which was the mean of 6 and 0 FFU/ml). The experiment was repeated with similar results.
[b]ND, not determined.

TABLE 15

Host Range of BIRV

| Species | Cell Type | LAPSN(BIRV)[a] Titer |
|---|---|---|
| Mouse (wild) | Mus dunni | $4 \times 10^4$ |
| Mouse (laboratory) | NIH 3T3 | $6 \times 10^3$ |
| Cat | G355 | $5 \times 10^4$ |
| Human | HDF | $3 \times 10^3$ |

[a]The indicated cells were infected with BIRV-pseudotype LAPSN and were stained for AP+ foci of cells two days after infection. Shown here are the titers of a population of cells producing LAPSN(BIRV). Similar results were obtained using a second, independently IdU-induced bulk population of cells producing BIRV.

MDEV shares a basic proviral structure with other retroviruses (LTR-gag-pol-env-LTR), but this virus is distinctly different from other retroviruses in several respects. The first unusual feature of MDEV is that it represents a novel murine viral interference group distinct from the amphotropic, xenotropic, ecotropic, polytropic, and 10A1 groups. In addition, MDEV does not interfere with SNV, MPMV, or GALV. Although MDEV appears to share a receptor with the RD114 virus in G355 cat cells, it does not do so in the other target cells tested. Not all of the four groups of endogenous viruses identified in Southeast Asian species of mice, as well as laboratory mouse-derived MMTV have been tested for interference patterns, and they have not been compared directly against MDEV. However, the prototype group C1 virus isolated from the Asian mouse *M. caroli* interferes with the infectious primate viruses GALV and SSAV (Callahan et al., (1978) supra.; Lieber et al. (1975) supra.). Although MDEV is also present in the genome of a wild Asian mouse, it does not interfere with GALV, and thus is distinct from the *M. caroli* virus. Some endogenous murine viruses isolated from laboratory mice have neither been cloned nor characterized with respect to their interference group, and direct comparison to MDEV has not been made. However, an endogenous virus (BIRV) has been activated from cells of the Balb/c mouse, a source for many of these murine virus studies (Aaronson et al., *Science* 174:57–159 (1971); Paran et al., *Proc. Natl. Acad. Sci. U.S.A.* 70:2391–2395 (1973); Todaro, *Perspect. Virol.* 8:81–101 (1973)). Interference analysis showed that BIRV does not interfere with MDEV, and that it most likely belongs to the polytropic group of viruses. These interference results indicate that MDEV uses a novel receptor for cell entry.

Beyond utilizing a unique receptor, MDEV is unusual with regard to its exceptionally large host range. MDEV is able to efficiently infect every cell type tested with the exception that Balb/c 3T3 cells were infected at a low level. Discrepant results in CCC-81 cells may relate to the variable interference of RD114 with MDEV infection, since cat cells carry and potentially could express the endogenous RD114 virus.

Finally, MDEV appears by hybridization analysis to have an unusual genome. Previous studies were not able to detect endogenous virus in *M. dunni* cells using either a reverse-transcriptase-polymerase chain reaction with primers to various parts of the env gene, which could detect xenotropic, ecotropic, polytropic and modified polytropic viruses (Irving et al., *Biotechnology* 11:1042–1046 (1993)), or by hybridization using probes for several MLV DNAs (Lander et al., *J. Virol.* 52:695–698 (1984)). As shown herein, MDEV does not hybridize to the genomes of any of the other viruses tested, including amphotropic, ecotropic, xenotropic, polytropic, 10A1, GALV, RD114, and MMTV. Furthermore, using the MDEV genome as a probe no related sequences were found in the genomic DNA of several animal species except in other mice. MDEV hybridization to genomic DNA of laboratory mice was limited to one faint band of about 9 kb that was present in all 3 mouse strains examined, indicating a single common integration site.

These results indicate that MDEV arose from an endogenous provirus present in *M. dunni* mice. MDEV appears to use a different receptor for cell entry than those of other retroviruses. The ability of MDEV to efficiently infect many types of human cells indicates that retrovirus packaging cells based on MDEV can be used for gene transfer purposes and human gene therapy applications.

Microorganism Deposit Information

The packaging cell line PD 227 was deposited with the American Type Culture Collection, 10801 University Boulevard, Manassas, Va. 20110-2209, May 5, 1998, under the conditions of the Budapest Treaty and designated accession number CRL-12525.

Although the foregoing invention has been described in some detail by way of illustration and example for purposes of clarity of understanding, it will be obvious that certain changes and modifications may be practiced within the scope of the invention. All publications and patents mentioned in this specification are herein incorporated by reference into the specification to the same extent as if each individual publication or patent was specifically and individually indicated to be incorporated herein by reference.

What is claimed is:

1. A cultured packaging cell for producing a replication-defective retroviral vector particle which binds to *Mus dunni* endogenous virus receptors, wherein the packaging cell is a vertebrate cell which can express and assemble retroviral proteins, comprising:
   a first vector encoding a retroviral envelope protein having the amino acid sequence of a *Mus dunni* endogenous virus envelope protein, or a fragment thereof, that directs the binding of the retroviral vector particle to *Mus dunni* endogenous virus retroviral receptors on a target cell; and
   a second vector encoding retrovirus Gag and Pol proteins, wherein upon expression of said retroviral envelope, Gag and Pol proteins in the packaging cell in the presence of a third vector having a sequence of a heterologous gene of interest, produces the replication-defective retroviral vector particle that binds to *Mus dunni* endogenous virus receptors of the target cell.

2. The cultured packaging cell of claim 1, wherein the first vector comprises an oligonucleotide sequence which encodes the amino acid sequence as depicted in SEQ ID NO:5.

3. The cultured packaging cell of claim 2, wherein the first vector comprises a nucleotide sequence as depicted in SEQ ID NO:1.

4. The cultured packaging cell of claim 2, wherein the *Mus dunni* endogenous virus envelope protein is a chimeric protein having non-*Mus dunni* envelope protein amino acid residues from a different retrovirus.

5. The cultured packaging cell of claim 4, wherein the retrovirus Gag and Pol proteins are from a Moloney murine leukemia virus.

6. A cultured packaging cell for producing a replication-defective retroviral vector particle which binds to *Mus dunni* endogenous virus receptors, wherein the packaging cell is a vertebrate cell which can express and assemble retroviral proteins, comprising:

a first vector encoding a retroviral envelope protein having the amino acid sequence of a *Mus dunni* endogenous virus envelope protein, or a fragment thereof, that directs the binding of the retroviral vector particle to *Mus dunni* endogenous virus retroviral receptors on a target cell; and a second vector encoding retrovirus Gag and Pol proteins; and a third vector comprising a nucleic acid sequence encoding a heterologous gene of interest, wherein upon expression of said retroviral envelope, Gag and Pol proteins in the packaging cell produces the replication-defective retroviral vector particle that binds to *Mus dunni* endogenous virus receptors of the target cell.

7. The cultured packaging cell of claim 6, wherein the heterologous gene encodes a protein, peptide, or RNA molecule.

8. The cultured packaging cell of claim 7, wherein the RNA molecule is an antisense RNA or a ribozyme.

9. The cultured packaging cell of claim 1, wherein the vertebrate cell is an avian or mammalian cell which can express and assemble retroviral proteins.

10. The cultured packaging cell of claim 1, wherein the first vector and the second vector are integrated in a chromosome of the packaging cell.

11. The cultured packaging cell line PD223 as deposited with the American Type Culture Collection and designated CRL-12525.

12. A cultured packaging cell for producing a replication-defective retroviral vector particle, wherein the packaging cell is a vertebrate cell which can express and assemble retroviral proteins, comprising:

a first vector comprising a *Mus dunni* endogenous virus envelope gene encoding the amino acid residue sequence as depicted in SEQ ID NO:5, or a fragment thereof, that directs binding of the retroviral vector particle to *Mus dunni* endogenous virus receptors on a target cell;

a second vector encoding retrovirus Gag and Pol proteins; and a third vector having a sequence comprising a heterologous gene of interest, wherein upon expression of said envelope gene and said Gag and Pol proteins in the packaging cell a replication-defective retroviral vector particle is produced that binds to *Mus dunni* endogenous virus receptors of the target cell.

* * * * *